(12) United States Patent
Zugmaier et al.

(10) Patent No.: US 9,192,665 B2
(45) Date of Patent: Nov. 24, 2015

(54) MEANS AND METHODS FOR TREATING DLBCL

(75) Inventors: Gerhard Zugmaier, Munich (DE); Dirk Nagorsen, Munich (DE); Juergen Scheele, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 26 days.

(21) Appl. No.: 13/881,889

(22) PCT Filed: Oct. 27, 2011

(86) PCT No.: PCT/EP2011/068851
§ 371 (c)(1),
(2), (4) Date: Jul. 18, 2013

(87) PCT Pub. No.: WO2012/055961
PCT Pub. Date: May 3, 2012

(65) Prior Publication Data
US 2013/0287778 A1    Oct. 31, 2013

Related U.S. Application Data

(60) Provisional application No. 61/407,107, filed on Oct. 27, 2010.

(51) Int. Cl.
*A61K 39/395* (2006.01)
*C07K 16/28* (2006.01)
*A61K 39/00* (2006.01)

(52) U.S. Cl.
CPC ....... *A61K 39/39558* (2013.01); *C07K 16/2803* (2013.01); *C07K 16/2809* (2013.01); *A61K 2039/505* (2013.01); *C07K 2317/31* (2013.01)

(58) Field of Classification Search
None
See application file for complete search history.

(56) References Cited

U.S. PATENT DOCUMENTS

2009/0191201 A1 * 7/2009 Heiss et al. ............... 424/136.1

FOREIGN PATENT DOCUMENTS

| WO | WO-2007/068354 A1 | 6/2007 |
| WO | WO-2011/051307 A1 | 5/2011 |

OTHER PUBLICATIONS

Ohshima et al. (Pathology International, 15:1-12, 2002).*
Bargou, et al., "Tumor Regression in Cancer Patients by Very Low Doses of a T Cell-Engaging Antibody," Science 321:974-977 (2008).
Dupire et al., "Targeted treatment and new agents in diffuse large B cell lymphoma," Int J Hematol 92:12-24 (2010).
Ng, "Diffuse Large B-Cell Lymphoma," Seminars in Radioation Oncology, 17(3):169-175 (2007).
Quintas, et al., "Investigational Immunotherapeutics for B-Cell Malignancies," Journal of Clinical Oncology 28(5):884-892 (2010).
Wilson et al., "Novel disease targets and management approaches for diffuse large B-cell lymphoma," Leukemia & Lymphoma 51(S1):1-10 (2010).
International Search Report from PCT/EP2011/068851 dated Apr. 18, 2012.

* cited by examiner

*Primary Examiner* — Misook Yu
*Assistant Examiner* — Nelson B Moseley, II
(74) *Attorney, Agent, or Firm* — Marshall, Gerstein & Borun LLP

(57) ABSTRACT

The present invention provides means and methods for treating diffuse large B cell lymphoma (DLBCL). Specifically, a bispecific CD19×CD3 antibody which engages T cells via its CD3 binding portion and concomitantly binds to CD19 on the surface of in particular, lymphoma cells via its CD19 binding portion (i.e. a bispecific T cell engager, "BiTE") is administered for use in the treatment of tumorous mass of lymophoreticular tissue and/or extranodal lymphoma caused by DLBCL in a patient.

19 Claims, No Drawings

MEANS AND METHODS FOR TREATING DLBCL

FIELD OF THE INVENTION

The present invention provides means and methods for treating diffuse large B cell lymphoma (DLBCL) with a CD3 binding antibody. Specifically, a bispecific CD19×CD3 antibody which engages T cells via its CD3 binding portion and concomitantly binds to CD19 on the surface of, in particular, lymphoma cells via its CD19 binding portion (i.e. a bispecific T cell engager, "BiTE") is applied for use in the treatment of tumorous mass of lymophoreticular tissue and/or extranodal lymphoma caused by DLBCL in a patient.

BACKGROUND OF THE INVENTION

Lymphoma is a cancer of lymphocytes. There are two main types of lymphoma: Hodgkin lymphoma (HL) and Non-Hodgkin lymphoma (NHL). Non-Hodgkin lymphoma (NHL) is the most common type of lymphoma. Although there are more than 30 types of NHL, diffuse large B-cell lymphoma (DLBCL) is the most common type, making up about 30 percent of all lymphomas. In the United States, DLBCL affects about 7 out of 100,000 people each year.

Diffuse large B-cell lymphoma is an aggressive lymphoma, sometimes termed as a high or intermediate grade lymphoma. That means that the lymphoma grows quickly, and can spread fast to different parts of the body. Diffuse large B-cell lymphoma mostly affects those above 50 years of age, though people of any age can get it. It is a bit more common in men than in women. About ⅔ of those who have diffuse large B-cell lymphoma have widespread disease at the time of diagnosis, extending to different parts of the body. In nearly half of the patients, the disease affects parts of the body outside the lymph nodes (called "extranodal" disease). The bone marrow is affected in about 10-20% of the patients. DLBCL is fatal if left untreated.

In DLBCL, the abnormal B-cell lymphocytes are larger than normal, and they have stopped responding to signals that usually limit the growth and reproduction of cells. DLBCL can either develop as a transformation from a less aggressive form of lymphoma or as a first occurrence of lymphoma (called de novo).

The first sign of DLBCL is often a quickly growing, non-painful mass in a lymph node in the neck, groin, or abdomen. Patients may also experience fever, weight loss, drenching night sweats, or other symptoms. In about 40 percent of cases, the cancer does not begin in the lymph nodes, but instead develops elsewhere. This is called extranodal disease. The most common site of extranodal involvement is the stomach or gastrointestinal tract, but the disease can arise in virtually any tissue. Most patients (about 60 percent) are not diagnosed with DLBCL until the disease is advanced (stage III or IV). In the remaining 40 percent of patients, the disease is confined to one side of the diaphragm (above or below the diaphragm). This is called localized disease.

Typically, the diagnosis of lymphoma is generally done with a lymph node biopsy. Once the diagnosis is confirmed, additional tests are performed to obtain more information about the extent to which the disease has spread in the body. This process is called staging. The results of these tests will help determine the most effective course of treatment.

The discussion of management of patients with diffuse large B-cell lymphoma can be conveniently divided into 3 groups: those presenting with localized disease, those presenting with disseminated disease, and those patients whose lymphoma recurs after an initial remission.

The standard treatment of advanced was and still is chemotherapy based on CHOP. CHOP consists of four chemotherapy drugs—Cyclophosphamide (also called Cytoxan/Neosar), Doxorubicin (also called Hydroxydaunorubicin) (or Adriamycin), Vincristine (Oncovin) and Prednisolone.

However, though the CHOP treatment was and is usually applied, the development of new treatment regimens including M-BACOD (methotrexate, bleomycin, doxorubicin, cyclophosphamide, vincristine, and dexamethasone), MACOP-B (methotrexate with leucovorin rescue doxorubicin, cyclophosphamide, vincristine, prednisone, and bleomycin) and ProMACE/CytaBOM (cyclophosphamide, doxorubicin, etoposide cytozar, bleomycin, vincristine, methotrexate prednisone) were reported to achieve results that seemed much better than had been observed with CHOP. These so-called third-generation regimens appeared to represent an important advance in therapy until an intergroup trial carried out in the United States demonstrated no superiority over CHOP.

Nevertheless, the CHOP therapy was expanded to a combination of chemotherapy and immunotherapy, i.e. R-CHOP. R-CHOP is a combination of drugs used in chemotherapy for aggressive Non-Hodgkin Lymphomas (NHL). It adds the drug Rituximab—a monoclonal antibody against CD20, to the standard combination called CHOP.

A commonly applied R-CHOP treatment regime is as follows: Rituximab is administered as an infusion over a few hours on the first day of treatment, while the drugs of the CHOP regimen may be started the next day. The entire course is usually repeated every three weeks for 6-8 cycles. The first three drugs of the CHOP chemotherapy regimen are usually given as injections or infusions in veins on a single day, while prednisolone is taken as pills for five days. Each cycle is repeated every 3 weeks for 6-8 cycles. CHOP chemotherapy is used for many of the common types of aggressive Non-Hodgkin Lymphomas including Diffuse Large B-Cell Lymphoma (DLBCL). Nowadays, R-CHOP can be considered the standard first line treatment for patients with DLBCL.

DHAP is a further combination of chemotherapeutic agents that is sometimes applied for the treatment of DLBCL. The DHAP chemotherapeutics include: Dexamethasone, cytarabine, which is sometimes called Ara-C and cisplatin, which contains platinum. DHAP can also be combined with Rituximab (tradename Rituxan®), i.e., R-DHAP.

ICE is another combination of chemotherapeutic agents that is sometimes applied for the treatment of DLBCL and named after the initials of the chemotherapy drugs used, which are: Ifosfamide, Carboplatin, and Etoposide. R-ICE also includes the monoclonal antibody drug Rituximab.

However, despite this major therapeutic advance, a significant proportion of patients will relapse or remain refractory to initial chemoimmunotherapy. Accordingly, there is a need for alternative and/or adjuvant therapies for the treatment of the aggressive and fast growing bulky tumor mass caused by DLBCL. Accordingly, the technical problem of the present invention is to comply with this need.

SUMMARY OF THE INVENTION

The present invention addresses this need and thus provides as a solution to the technical problem embodiments pertaining to means and methods for use in the treatment of tumorous mass of lymph node tissue and/or extranodal lymphoma caused by diffuse large B cell lymphoma (DLBCL) in a patient in that a composition comprising a CD19×CD3 bispecific antibody is applied. An example of a CD19×CD3 bispecific (single chain) antibody is Blinatumomab (MT103).

Blinatumomab is a lymphoma-directed, recombinant bispecific single-chain CD19×CD3 antibody that binds to CD19 on the surface of almost all B cells and B tumor cells and concomitantly can engage a T cell, thereby triggering the T-cell to kill the target B cell or B tumor cell. It is thus a so-called BiTE® (Bispecific T-cell Engager) antibody. Blinatumomab consists of four immunoglobulin variable domains assembled into a single polypeptide chain. Two of the variable domains form the binding site for CD19, a cell surface antigen expressed on most B cells and B tumor cells. The other two variable domains form the binding site for CD3 epsilon of the CD3 complex on T cells. Blinatumomab is designed to direct the body's cytotoxic, or cell-destroying, T cells against tumor cells, and is presently in clinical trials.

Though WO 2007/068354 mentions that a CD19×CD3 bispecific antibody could be used amongst different B-cell non-Hodgkin lymphomas, for the treatment of DLBCL, this document does not allow any conclusion to be drawn with regard to the actual existence of a therapeutic effect or any pharmacological effect which directly and unambiguously underlays the claimed therapeutic application of a CD19×CD3 bispecific antibody.

This is even more true when switching to the difficult to-treat and aggressive DLBCL.

However, to their surprise, the present inventors have found that a CD19×CD3 bispecific antibody is beneficial in the treatment of tumorous mass of lymphoreticular tissue (also referred to herein as lymph node tissue) and/or extranodal lymphoma caused by diffuse large B cell lymphoma (DLBCL) in a patient. Indeed, in clinical trials it was observed that a CD19×CD3 bispecific antibody led to outstanding results in the treatment of patients suffering from DLBCL in that in some patients a tremendous debulking of tumorous mass was observed, already after only a few weeks administration. Of note, the patients treated with a CD19×CD3 bispecific antibody were heavily pre-treated with a combination of various chemotherapeutics, either with the combination of chemotherapeutics or with that combination together with the CD20—specific antibody Rituximab. However, the immunotherapy with a CD19×CD3 bispecific antibody as the sole therapeutic agent in DLBCL patients resulted in partial remission or even complete remission (see the appended Examples, in particular patients 153-001, 135-001 and 109-038).

In sum, the outstanding results observed by the present inventors in their clinical trials could not have been expected, since in the therapy of cancer, in particular lymphomas, no one-fits-all drug ("magic bullet") is available and, thus, for each and every clinical trial, so to say, no reasonable expectation of success exists, for which reason a skilled artisan is highly cautious and would never simply try out an experimental drug in a human patient. Yet, the present inventors with their profound knowledge and preclinical data on a CD19×CD3 bispecific antibody took the risk and treated, more or less, treatment-resistant DLBCL patients and were successful. Accordingly, a CD19×CD3 bispecific antibody may therefore pave the way for a novel treatment of DLBCL.

Aspects of the present invention are:
1. A composition comprising a CD19×CD3 bispecific antibody for use in (a method for) the treatment of tumorous mass of lymph node tissue and/or extranodal lymphoma caused by diffuse large B cell lymphoma (DLBCL) in a patient. Also a method of treatment of tumorous mass of lymph node tissue and/or extranodal lymphoma caused by DLBCL comprising administering to a patient afflicted with DLBCL, an effective amount of a CD19×CD3 bispecific antibody.
2. The composition or method of item 1, wherein the tumorous mass is characterized by tumours having a size of more than 10×10 mm.
3. The composition or method of item 1 or 2, wherein the lymph node tissue includes lymph nodes and/or spleen.
4. The composition or method of item 1 or 2, wherein the extranodal lymphoma includes central nervous system (CNS), cutaneous tissue, breast, lungs, liver, gastrointestinal tract, genitourinary tract, ocular tissue, bone marrow and/or bones.
5. The composition or method of any one of the preceding items, wherein a first dose of the composition is administered for a first period of time and consecutively a second dose of the composition is administered for a second period of time, wherein the second dose exceeds the first dose.
6. The composition or method of any one of the preceding items, wherein said first period of time exceeds 3 days.
7. The composition or method of any one of the preceding items, wherein said first period of time is between 3 days and 10 days.
8. The composition or method of any one of the preceding items, wherein said second period of time exceeds 18 days.
9. The composition or method of any one of the preceding items, wherein said second period of time is between 18 days and 81 days, 21 or 49 days being preferred.
10. The composition or method of any one of the preceding items, wherein said first period of time is between 3 days and 10 days, and said second period of time is between 18 days and 81 days.
11. The composition or method of item 10, wherein said first period of time is 7 days and said second period of time is 21 or 49 days.
12. The composition of any one of the preceding items, wherein said first dose is between 1 and 15 µg/m²/d, 5, 10 or 15 µg/m²/d being preferred.
13. The composition or method of any one of the preceding items, wherein said second dose is between 15 and 60 µg/m²/d, 60 µg/m²/d being preferred.
14. The composition or method of item 5, further comprising administering after a first and second dose for a first and second period of time a third dose of the composition for a third period of time.
15. The composition or method of item 14, wherein the third period of time exceeds the first and second period of time, whereby thesecond dose exceeds said first dose.
16. The composition or method of item 14 or 15, wherein the third dose exceeds the first and second dose
17. The composition or method of any one of items 14 to 16, wherein said first period of time exceeds 3 days.
18. The composition or method of any one of items 14 to 17, wherein said first period of time is between 3 days and 10 days, with 7 days being preferred.
19. The composition or method of item 14, wherein said second period of time exceeds 3 days.
20. The composition or method of any one of items 14 to 19, wherein said second period of time is between 3 days and 10 days, with 7 days being preferred.
21. The composition or method of item 14, wherein said third period of time exceeds 8 days.
22. The composition or method of any one of items 14 to 21, wherein said third period of time is between 8 days and 78 days, with 14 or 42 days being preferred
23. The composition or method of any one of items 14 to 22, wherein said first period of time is between 3 days and 10 days, and said second period of time is between 3 days and 10 days, and said third period of time is between 8 days and 78 days 24. The composition or method of item 23, wherein said first period of time is 7 days, said second period of time is 7 days and said third period of time is 14 or 42 days.
25. The composition or method of any one of items 14 to 24, wherein said first dose is between 1 and 15 µg/m²/d, 5 µg/m²/d being preferred.
26. The composition or method of any one of items 14 to 25, wherein said second dose is between 1 and 15 µg/m²/d, 15 µg/m²/d being preferred.
27. The composition or method of any one of items 14 to 26, wherein said third dose is between 15 and 60 µg/m²/d or 15 and 90 µg/m²/d or 15 and 120 µg/m²/d, with 60 µg/m²/d being preferred.
28. The composition or method of any one of the preceding items, wherein the composition further comprises at least one chemotherapeutic agent.
29. A composition of any one of the preceding items for use in a method of treating tumor mass of lymph node tissue and/or extranodal lymphoma caused by diffuse large B cell lymphoma (DLBCL) in a patient in need thereof, comprising administering a therapeutically effective amount of the composition to the patient in need thereof.
30. A pharmaceutical kit for treating tumor mass of lymph node tissue and/or extranodal lymphoma caused by diffuse large B cell lymphoma (DLBCL) in a patient comprising a composition of any one of the preceding items and optionally means for instructions (instruction sheet).
31. Use of a composition of any one of the preceding items for the preparation of a pharmaceutical composition for treating tumor mass of lymph node tissue and/or extranodal lymphoma caused by diffuse large B cell lymphoma (DLBCL).
32. A pharmaceutical package or kit comprising the first dose and the second dose as defined in any one of the preceding items.
33. The pharmaceutical package or kit of item 32, further comprising a third dose as defined in any one of the preceding items.
34. The pharmaceutical package or kit of item 32 or 33, further comprising means to administer the first and/or the second and/or third dose to a patient.

+++

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

The discussion of the general methods given herein is intended for illustrative purposes only. Other alternative methods and embodiments will be apparent to those of skill in the art upon review of this disclosure.

A group of items linked with the conjunction "or" should not be read as requiring mutual exclusivity among that group, but rather should also be read as "and/or" unless expressly stated otherwise.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As described herein, "preferred embodiment" means "preferred embodiment of the present invention". Likewise, as described herein, "various embodiments" and "another embodiment" means "various embodiments of the present invention" and "another embodiment of the present invention", respectively.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

+++

DETAILED DESCRIPTION OF THE INVENTION

It is apparent that either chemotherapy alone or chemotherapy in combination with immunotherapy is applied in the art for the treatment of DLBCL. However, an antibody such as Rituximab (a CD20-specific antibody) is not usually applied as single compound for the treatment of DLBCL, probably because DLBCL is an aggressive, fast growing lymphoma for which it cannot be expected that an antibody alone which requires immune (effector) cells in order to exert CDC and/or ADCC is efficient in monotherapy. Accordingly, usually a combination of chemotherapeutics is aplied together with Rituximab. In addition, it was observed that Rituximab might not have the desired therapeutic effect if B-cells are not Bcl-2 positive (Armitage (2007), Blood 110(1):29-36). Thus, Rituximab might under certain circumstances have a somewhat limited therapeutic spectrum.

Moreover, oftentimes DLBCL represents as bulky tumor mass and it can be reasonably assumed that a conventional Ig antibody might not be capable of efficiently penetrating bulky tumor mass and might thus not be able to attract effector cells which could then kill tumor cells. This is so because, Rituximab, for example, requires effector cells of the immune system which might not be available in sufficient quantity or quality, since patients are oftentimes heavily pre-treated with chemotherapeutics that also harm immune cells. Thus, it would be desirable to have an antibody available that efficiently attracts (engages) immune cells that kill tumor cells. The present invention, by way of a CD19×CD3 bispecific (single chain) antibody provides such an antibody. In fact, in clinical trials, the present inventors observed to their surprise that a CD19×CD3 bispecific (single chain) antibody as the sole therapeutic agent successfully reduced tumorous mass of lymph node tissue and/or extranodal lymphoma caused by DLBCL. In fact, even tumors having a size of up to 63×47 mm or more were reduced and even completely eliminated. This outstanding result could not have been expected, since, for example, Rituximab is not applied in the art as the sole therapeutic agent. Rather, it is applied together with a combination of chemotherapeutics.

The present inventors did not only have to deal with the task of treating an aggressive, rapidly growing lymphoma in patients, who were heavily pre-treated with chemotherapy or a combination of chemotherapy with immunotherapy (even with a powerful CD20-specific antibody) and suffered, at least partly, from heavy tumor burden when applying a CD19×CD3 bispecific antibody as the sole therapeutic agent, but they also had to solve the problem of ameliorating, preferably preventing adverse effects that were previously observed with the bispecific antibody. In other words, the present inventors on the one hand had to observe the development and even the onset of tumor progression after prior (immuno)chemotherapy to chemotherapy in patients suffering from DLBCL (patients were pre-treated with chemotherapy and chemoimmunotherapy), and on the other hand they had to observe dose limiting toxicity.

In fact, as described for instance in WO 99/54440, adverse effects have been observed in a previous study performed with the CD19×CD3 antibody, Blinatumomab (applied in repeated bolus infusions to a patient with B-cell derived chronic lymphatic leukaemia (B-CLL). Specifically, in a clinical trial 7 out of 22 patients showed an early neurological/psychiatric reaction, including, for example, confusion, ataxia, speech disorder, or disorientation.

In order to try to better manage these undesired side effects, the mode of administration of the CD19×CD3 bispecific single chain antibody has been changed in that it has been switched over from bolus infusion to a continuous intravenous administration of said antibody for a longer period of time. However, neurological/psychiatric reactions have still been found in the course of that clinical trial.

Thus, for the clinical trials in connection with the application of a CD19×CD3 bispecific single chain antibody for the treatment of tumorous mass of lymph node tissue and/or extranodal lymphoma caused by DLBCL, the present inventors had to develop a treatment regime which was efficient and would be well tolerated by most of the patients. To this end, the present inventors applied a step-wise application of a CD19×CD3 bispecific single chain antibody in that 5/15/60 $\mu g/m^2/24$ h was administered to patients. Thereby, adverse effects, in particular neurological/psychiatric events could be reduced in number, ameliorated and even prevented. Also contemplated in the step-wise administration of a CD19×CD3 bispecific single chain antibody is a treatment regime using two of the dosages, such as 5/15 $\mu g/m^2/24$ h, 5/60 $\mu g/m^2/24$ h, or 15/60 $\mu g/m^2/24$ h for the duration of the patient's treatment. The appropriate dosage can be selected by the clinician on the basis of efficacy, tolerability and safety with a minimum of adverse effects in the patient.

But the inventors also contemplate the treatment of tumorous mass of lymph node tissue and/or extranodal lymphoma caused by DLBCL to include the continuous administration of a flat dose without escalation to a subsequent higher dose. For example, the present treatment regime includes the administration of 5 $\mu g/m^2/24$ h, 15 $\mu g/m^2/24$ h, or 60 $\mu g/m^2/24$ h of a CD19×CD3 bispecific single chain antibody until the conclusion of a course of the treatment up to 8 weeks [56 days] with good tolerability and no adverse effects, and even longer if determined to be safe and effective.

It is also envisaged that the methods of the present invention are further characterized by the administration of a glucocorticoid. This administration occurs prior to and optionally during the administration of a CD19×CD3 bispecific single chain antibody in the DLBCL patient. This concomitant administration may occur for one or more consecutive days after the administration of the antibody and optionally during the continued treatment with the antibody.

As it is shown in the Examples, glucocorticoids were found to ameliorate and/or prevent neurological reactions in the course of the methods of treatment of the present invention. It is therefore envisaged that the methods of the present invention (and thereby the dosage regimens of the present invention) are further characterized by the optional administration of at least one glucocorticoid. Said administration is preferably prior to the first treatment with the antibody, and then concomitantly on the second and third days after the start of treatment, and may also be administered later during treatment should any neurological adverse event(s) occur. If the treatment regime includes a dose escalation according to the dosing schedule, described herein, then the glucocorticoid is administered prior to each dose escalation and concomitantly on the following second and third days after each new escalated dose, and optionally on additional days to treat any neurological adverse event.

Glucocorticoids (GC) are a class of steroid hormones that bind to the glucocorticoid receptor (GR), which is present in almost every vertebrate animal cell, including humans. These compounds are potent anti-inflammatory agents, regardless of the inflammation's cause. Glucocorticoids suppress, inter alia, the cell-mediated immunity by inhibiting genes that code for the cytokines IL-1, IL-2, IL-3, IL-4, IL-5, IL-6, IL-8 and IFN-γ.

As used herein, the term "glucocorticoid" comprises at least cortisone, cortisol, cloprednol, prednisone, prednisolone, methylprednisolone, deflazacort, fluocortolone, triamcinolone, dexamethasone, and betamethasone, flusticasonepropionate, triamcinolonacetonide. Dexamethasone is preferred and its preferred dosage range is between 6 to 40 mg per dose.

Dexamethasone has the highest glucocorticoid potency of the most commonly used steroids and also has the longest half-life (see Table below). But a person skilled in the field can select one of the other known glucocorticoids, some of which are disclosed herein, and select an appropriate effective dose to ameliorate or prevent neurological adverse events that may result from the treatment of a DLBCL patient with a CD19×CD3 bispecific single chain antibody.

| Agent | Approx. equiv. dose (mg) | Relative anti-inflammatory (gluco-corticoid) potency | Relative mineralo-corticoid ($Na^+$ retaining) potency | Biologic half-life (hrs) |
|---|---|---|---|---|
| Cortisone | 25 | 0.8 | 0.8 | 8-12 |
| Hydrocortisone | 20 | 1 | 1 | 8-12 |
| Prednisone | 5 | 4 | 0.8 | 18-36 |
| Prednisolone | 5 | 4 | 0.8 | 18-36 |
| Methyl-prednisolone | 5 | 5 | 0.5 | 18-36 |
| Dexamethasone | 0.75 | 25 | 0 | 36-54 |

Dexamethasone also possesses a beneficial effect in malignant central nervous system (CNS) disease (e.g. CNS lymphoma or brain metastases)—possibly due to specific penetration to the CNS. It is also preferentially (over other steroids) used to treat brain edema. Although corticosteroids decrease capillary permeability in the tumor itself, it has been found in animal models that dexamethasone may act differently and decrease edema by effects on bulk flow away from the tumor (Molnar, Lapin, & Goothuis, 1995, Neurooncol. 1995; 25(1):19-28).

The present inventors with the aim of further reducing and/or preventing adverse effects found that the (intermittent) administration of dexamethasone during the increase of the doses of the CD19×CD3 bispecific single chain antibody could contribute to a further amelioration and/or prevention of neurological reactions. In particular, dexamethasone was administered for a period of three days during which the dose of the CD19×CD3 bispecific (single chain) antibody was increased. More specifically, dexamethasone was administered at day 1 in a dose of 24 µg, at day 2 in a dose of 16 µg and at day 3 in a dose of 8 (see also Example 8). Though it is known that dexamethasone reduces the activity of immune cells including T-cells ($CD4^+$ and $CD8^+$ T-cells), since it is a known immunosuppressant, and it could thus have been expected that the CD19×CD3 bispecific antibody might not engage potent (active) T-cells, the present inventors observed the opposite. Indeed, the T-cells engaged by the CD19×CD3 bispecific antibody were apparently potent, since an outstanding reduction of tumor mass was observed in the clinical trials with DLBCL patients (see the appended Examples).

In view of the successful treatment of the tumorous mass of DLBCL patients in a clinical trial with a CD19×CD3 bispecific antibody, the present invention provides in a first aspect a composition comprising a CD19×CD3 bispecific antibody for use in the treatment of tumorous mass of lymph node tissue and/or extranodal lymphoma caused by diffuse large B cell lymphoma (DLBCL) in a patient.

Likewise, in the alternative, the present invention provides for a composition comprising a CD19×CD3 bispecific antibody for use in a method of treating tumor mass of lymph node tissue and/or extranodal lymphoma caused by diffuse large B cell lymphoma (DLBCL) in a patient in need thereof, comprising administering a therapeutically effective amount of the composition to the patient in need thereof.

Also, in the alternative, the present invention provides for a use of a composition comprising a CD19×CD3 bispecific antibody for the preparation of a pharmaceutical composition for treating tumor mass of lymphoreticular tissue and/or extranodal lymphoma caused by diffuse large B cell lymphoma (DLBCL).

Further, in the alternative, the present invention provides a method of treating tumorous mass of lymph node tissue and/or extranodal lymphoma caused by diffuse large B cell lymphoma (DLBCL) in a patient, comprising administering a therapeutically effective amount of a CD19×CD3 bispecific antibody to said patient. The antibody preferably is contained in a composition, which preferably is a pharmaceutical composition.

DLBCL is a neoplasia of lymph node tissue, developing from B-cells. It is clinically, morphologically and genetically a heterogeneous group of malignant proliferation of large lymphoid B cells that accounts for approximately 40% (25,000 cases/year) of adult non-Hodgkin lymphomas. Two prognostically different subgroups of DLBCL have been identified with distinct gene expression profiles either characteristic of normal germinal center B cells or of activated memory B cells. The germinal center B-cell-like (GC) subgroup was correlated with a significantly better prognosis (5-year survival: 76%) in comparison to the activated B-cell-like (ABC or non-GC) subgroup (5-year survival: 16%) (Alizadeh et al. (2000) Nature 403:503-511, Shipp et al. (2002) Nat Med 8:68-74).

The first sign (symptom) of DLBCL is often a quickly growing, non-painful mass in a lymph node in the neck, groin, or abdomen. Patients may also experience fever, weight loss, drenching night sweats, or other symptoms.

As used herein, a "CD19×CD3 bispecific antibody" (including a CD19×CD3 bispecific single chain antibody—sometimes both terms are used interchangeably herein) denotes a single polypeptide chain comprising two binding domains. Such CD19×CD3 bispecific single chain antibodies are preferred in the context of the methods/dosage regimen of the present invention. Each binding domain comprises at least one variable region from an antibody heavy chain ("VH or H region"), wherein the VH region of the first binding domain specifically binds to the CD3 epsilon molecule, and the VH region of the second binding domain specifically binds to CD19. The two binding domains are optionally linked to one another by a short polypeptide spacer. A non-limiting example for a polypeptide spacer is Gly-Gly-Gly-Gly-Ser (G-G-G-G-S) and repeats thereof. Each binding domain may additionally comprise one variable region from an antibody light chain ("VL or L region"), the VH region and VL region within each of the first and second binding domains being linked to one another via a polypeptide linker, for example of the type disclosed and claimed in EP 623679 B1, but in any case long enough to allow the VH region and VL region of the first binding domain and the VH region and VL region of the second binding domain to pair with one another such that, together, they are able to specifically bind to the respective first and second binding domains. Such CD19CD3 bispecific single chain antibodies are described in great detail in WO 99/54440 and WO 2004/106381 and WO2008/119565.

The term "binding domain" characterizes in connection with the present invention a domain of a polypeptide which specifically binds to/interacts with a given target structure/antigen/epitope. Thus, the binding domain is an "antigen-interaction-site". The term "antigen-interaction-site" defines, in accordance with the present invention, a motif of a polypeptide, which is able to specifically interact with a specific antigen or a specific group of antigens, e.g. the identical antigen in different species. Said binding/interaction is also understood to define a "specific recognition". The term "specifically recognizing" means in accordance with this invention that the antibody molecule is capable of specifically interacting with and/or binding to at least two, preferably at least three, more preferably at least four amino acids of an antigen, e.g. the human CD3 antigen as defined herein. Such binding may be exemplified by the specificity of a "lock-and-key-principle". Thus, specific motifs in the amino acid sequence of the binding domain and the antigen bind to each other as a result of their primary, secondary or tertiary structure as well as the result of secondary modifications of said structure. The specific interaction of the antigen-interaction-site with its specific antigen may result as well in a simple binding of said site to the antigen. Moreover, the specific interaction of the binding domain/antigen-interaction-site with its specific antigen may alternatively result in the initiation of a signal, e.g. due to the induction of a change of the conformation of the antigen, an oligomerization of the antigen, etc. A preferred example of a binding domain in line with the present invention is an antibody. The binding domain may be a monoclonal or polyclonal antibody or derived from a monoclonal or polyclonal antibody. The term "antibody" comprises derivatives or functional fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also comprises immunoglobulins (Ig's) of different classes (i.e. IgA, IgG, IgM, IgD and IgE) and subclasses (such as IgG1, IgG2 etc.).

The definition of the term "antibody" also includes embodiments such as chimeric, single chain and humanized antibodies, as well as antibody fragments, like, inter alia, Fab fragments. Antibody fragments or derivatives further comprise F(ab')2, Fv, scFv fragments or single domain antibodies, single variable domain antibodies or immunoglobulin single variable domain comprising merely one variable domain, which might be VH or VL, that specifically bind to an antigen or epitope independently of other V regions or domains; see, for example, Harlow and Lane (1988) and (1999), cited above. Such immunoglobulin single variable domain encompasses not only an isolated antibody single variable domain polypeptide, but also larger polypeptides that comprise one or more monomers of an antibody single variable domain polypeptide sequence. As used herein, CD3 epsilon denotes a molecule expressed as part of the T cell receptor and has the meaning as typically ascribed to it in the prior art. In human, it encompasses in individual or independently combined form all known CD3 subunits, for example CD3 epsilon, CD3 delta, CD3 gamma, CD3 zeta, CD3 alpha and CD3 beta. The human CD3 epsilon is indicated in GenBank Accession No.NM_000733.

The human CD19 protein is indicated in GenBank Accession No. AAA69966.

Preferably, the bispecific antibody applied in the methods/dosage regimens of the present invention has the domain arrangement VL(CD19)-VH(CD19)-VH(CD3)-VL(CD3).

It is, however, also envisaged that the methods of the invention can be carried out with CD19xCD3 bispecific single chain antibodies of other domain arrangements, such as VH(CD19)-VL(CD19)-VH(CD3)-VL(CD3),
VL(CD19)-VH(CD19)-VL(CD3)-VH(CD3),
VH(CD19)-VL(CD19)-VL(CD3)-VH(CD3),
VL(CD3)-VH(CD3)-VH(CD19)-VL(CD19),
VH(CD3)-VL(CD3)-VH(CD19)-VL(CD19),
VL(CD3)-VH(CD3)-VL(CD19)-VH(CD19), or
VH(CD3)-VL(CD3)-VL(CD19)-VH(CD19).

A preferred CD19xCD3 bispecific antibody applied in the methods of the present invention comprises the
(a) anti-CD3 CDRs of the heavy chain shown as CD3 CDR-H1 in SEQ ID NO: 11 (GYTFTRYTMH), CD3 CDR-H2 in SEQ ID NO: 12 (YINPSRGYTNYNQKFKD) and CD3 CDR-H3 in SEQ ID NO: 13 (YYDDHYCLDY); and/or
(b) anti-CD3 CDRs of the light chain shown as CD3 CDR-L1 in SEQ ID NO: 14 (RASSSVSYMN), CD3 CDR-L2 in SEQ ID NO: 15 (DTSKVAS) and CD3 CDR-L3 in SEQ ID NO: 16 (QQWSSNPLT); and/or
(c) anti-CD19 CDRs of the heavy chain shown as CD19 CDR-H1 in SEQ ID NO: 17 (GYAFSSYWMN), CD19 CDR-H2 in SEQ ID NO: 18 (QIWPGDGDTNYNGKFKG) and CD19 CDR-H3 in SEQ ID NO: 19 (RETTTVGRYYYAMDY); and/or
(d) anti-CD19 CDRs of the light chain shown as CD19 CDR-L1 in SEQ ID NO: 20 (KASQSVDYDGDSYLN), CD19 CDR-L2 in SEQ ID NO: 21 (DASNLVS) and CD19 CDR-L3 in SEQ ID NO: 22 (QQSTEDPWT).

It is more preferred that the CD19xCD3 bispecific single chain antibody applied in the methods of the present invention comprises the CD3 CDRs of the heavy and light chain. Even more preferably, the CD19xCD3 bispecific antibody applied in the methods of the present invention comprises the CD3 CDRs of the heavy and light chain as well as the CD19 CDRs of the heavy and light chain.

The CDRs referred to herein are in accordance with the Kabat numbering system. The Kabat numbering scheme is a widely adopted standard for numbering the residues in an antibody in a consistent manner (Kabat et al., Sequences of Proteins of Immunological Interest, 1991).

Alternatively, it is preferred that the CD19xCD3 bispecific single chain antibody applied in the methods of the present invention comprises the
(a) CD19 variable heavy chain shown in SEQ ID NO: 3 (nucleotide sequence is shown in SEQ ID NO: 4); and/or
(b) CD19 variable light chain shown in SEQ ID NO: 5 (nucleotide sequence is shown in SEQ ID NO: 6); and/or
(c) CD3 variable heavy chain shown in SEQ ID NO: 7 (nucleotide sequence is shown in SEQ ID NO: 8); and/or
(d) CD3 variable light chain shown in SEQ ID NO: 9 (nucleotide sequence is shown in SEQ ID NO: 10).

More preferably, the CD19xCD3 bispecific single chain antibody applied in the methods of the present invention comprises the CD19 variable heavy and light chain and/or the CD3 variable heavy and light chain. Even more preferably, the CD19xCD3 bispecific single chain antibody applied in the methods of the present invention comprises the CD19 variable heavy and light chain as well as the CD3 variable heavy and light chain. In another alternative, it is also preferred that said bispecific single chain antibody comprises an amino acid sequence selected from the group consisting of
(a) an amino acid sequence as depicted in SEQ ID NO: 1;
(b) an amino acid sequence encoded by a nucleic acid sequence as shown in SEQ ID NO: 2;
(c) an amino acid sequence encoded by a nucleic acid sequence having at least 70%, 80%, 90%, 95% or 99% identity to a nucleic acid sequence of (b), wherein said amino acid sequence is capable of specifically binding to CD3 and CD19; and
(d) an amino acid sequence encoded by a nucleic acid sequence which is degenerate as a result of the genetic code to a nucleotide sequence of (b), wherein said amino acid sequence is capable of specifically binding to CD3 and CD19.

It is to be understood that the sequence identity is determined over the entire amino acid sequence. For sequence alignments, for example, the programs Gap or BestFit can be used (Needleman and Wunsch J. Mol. Biol. 48 (1970), 443-453; Smith and Waterman, Adv. Appl. Math 2 (1981), 482-489), which is contained in the GCG software package (Genetics Computer Group, 575 Science Drive, Madison, Wis., USA 53711 (1991). It is a routine method for those skilled in the art to determine and identify an amino acid sequence having e.g. 70%, 80%, 90%, 95%, 96%, 97%, 98% or 99% sequence identity to the amino acid sequences of the CD19×CD3 bispecific antibody described herein (preferably MT103). For example, according to Crick's Wobble hypothesis, the 5' base on the anti-codon is not as spatially confined as the other two bases, and could thus have non-standard base pairing. Put in other words: the third position in a codon triplet may vary so that two triplets which differ in this third position may encode the same amino acid residue. Said hypothesis is well known to the person skilled in the art (see e.g. http://en.wikipedia.org/wiki/Wobble_Hypothesis; Crick, J Mol Biol 19 (1966): 548-55). It is furthermore a routine procedure for those skilled in the art to determine cytotoxic activity of such an amino acid sequence having e.g. 70%, 80%, 90%, 95%, 96%, 97%, 98% or 99% A sequence identity to the nucleotide or amino acid sequences of the CD19×CD3 bispecific single chain antibody described herein. Cytotoxic activity of the CD19×CD3 bispecific single chain antibody or an antibody construct having e.g. 70%, 80%, 90%, 95%, 96%, 97%, 98% or 99% A sequence identity to the amino acid sequences of the CD19×CD3 bispecific single chain antibody can be determined by methods as illustrated e.g. in WO 99/54440.

Particularly preferred, said CD19×CD3 bispecific single chain antibody has the amino acid sequence shown in SEQ ID NO: 1.

Also particularly preferred is the CD19×CD3 bispecific antibody MT103 described in WO 99/54440 as well as those CD19×CD3 bispecific antibodies described in WO 2004/106381 or WO2008/119565.

Further particularly preferred is the CD19×CD3 bispecific antibody described in WO2008/119565. The CD3 binding moiety of this bispecific antibody is capable of binding to human and non-human primates such as rhesus apes and macaques, thereby conferring cross-species specific reactivity. Accordingly, it can be used for both pre-clinical and clinical studies, which is highly advantageous, since no surrogate antibodies are required and the results obtained in pre-clinical studies can be directly applied and adapted for use in humans.

Typically, the diagnosis of lymphoma, is generally done in a sample obtained from a patient suspected to develop and/or have a lymphoma, in particular DLBCL.

In accordance with the present invention by the term "sample" is intended any biological sample obtained from a human patient containing polynucleotides or polypeptides or portions thereof. Biological samples include body fluids (such as blood, serum, plasma, urine, saliva, synovial fluid and spinal fluid) and tissue sources found to malignant CD19 positive lymphocytes. Methods for obtaining tissue biopsies and body fluids from patients are well known in the art. Generally, a biological sample which includes peripheral blood mononuclear cells (PBMCs), in particular B cells and T cells is preferred as a source.

A sample which includes peripheral blood mononuclear cells (PBMCs), in particular B cells and T cells, is preferably taken from peripheral blood of a human patient. Other preferred samples are whole blood, serum, plasma or synovial fluid, with plasma or serum being most preferred.

Another preferred sample obtained from a patient is a lymph node biopsy. A lymph node biopsy is, for example, obtained with an excisional biopsy of an abnormal lymph node or a generous incisional biopsy of an involved organ. In some cases, cutting-needle biopsies can provide adequate tissue for diagnosis. In addition, an adequate bone marrow biopsy may be performed. Diagnosis can be supplemented by gene-expression profiling. More preferably, the diagnosis is preferably made by a hematopathologist with experience in diagnosing lymphomas, in particular DLBCL by, preferably applying the WHO classification of lymphoid neoplasma (see Table 1 on page 30 of the publication of Armitage in Blood (2007), Vol. 110 (1):29-36). It is sometimes also preferred to perform immunohistochemistry and on occasion to apply cytogenetics or fluorescent in situ hybridisation (FISH) in order to clarify an initial diagnosis.

Given that, it is a preferred embodiment of the present invention that DLCBL is diagnosed in accordance with the afore described symptoms and/or by applying the afore described means and methods such as lymph node biopsy, immunohistochemistry, cytogenetics, gene-profiling and/or FISH.

Once the diagnosis is made and, preferably confirmed, additional tests such as restaging by re-biopsy by a further experienced hematopathologist and/or further imaging studies including computer tomography, ultra sound imaging, and/or PET scan of the chest, abdomen and/or pelvis, are performed to obtain more information about the extent to which the disease has spread in the body. This process is called staging. The results of these tests will help determine the most effective course of treatment.

A number of staging tests are available to help determine which areas of the body have been affected by follicular lymphoma. Tests that may be done include: CT scan, blood tests, bone marrow biopsy and/or PET scan.

Staging involves dividing patients into groups (stages) based upon how much of the lymphatic system is involved at the time of diagnosis. Staging helps determine a person's prognosis and treatment options.

Stages of lymphoma can be defined as follows:
Stage I—Only one lymph node region is involved, or only one lymph structure is involved.
Stage II—Two or more lymph node regions or lymph node structures on the same side of the diaphragm are involved.
Stage III—Lymph node regions or structures on both sides of the diaphragm are involved.
Stage IV—There is widespread involvement of a number of organs or tissues other than lymph node regions or structures, such as the liver, lung, or bone marrow.
When a stage is assigned, it also includes a letter, A or B, to denote whether fever, weight loss, or night sweats are present. "A" means these symptoms are not present; "B" means they are. For example, a person with stage 1B disease has evidence of cancer in one lymph node region and has "B" symptoms (fever, weight loss, or night sweats).

In the present invention, DLBCL is preferably staged in accordance with the criteria set out in Cheson et al. (2007), J. Clin. Oncol. 25(5):579-586.

When used herein a "composition comprising a CD19×CD3 bispecific antibody" encompasses preferably a pharmaceutical composition. Thus, the CD19×CD3 bispecific antibody is preferably in the form of a medicament. Accordingly, the term "pharmaceutical composition" and "medicament" when used herein are interchangeable.

In this specification the term "pharmaceutical" shall have its widest meaning and include compound(s) used in the treatment of DLBCL in a patient. Preferably the compound used in the treatment of DLCBL is a CD19×CD3 bispecific antibody. Accordingly, a pharmaceutical composition preferably comprises a CD19×CD3 bispecific antibody and, optionally, a pharmaceutically acceptable carrier.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.
Proper fluidity may be maintained, for example, by the use of coating materials, such as lecithin, by the maintenance of the required particle size in the case of dispersions, and by the use of surfactants.

Pharmaceutical compositions containing the antibodies may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Pharmaceutical compositions of the present invention may also comprise isotonicity agents, such as sugars, polyalcohols such as mannitol, sorbitol, glycerol or sodium chloride in the compositions.

Pharmaceutically acceptable diluents include saline and aqueous buffer solutions. The pharmaceutical compositions containing the antibodies may also contain one or more adjuvants appropriate for the chosen route of administration, such as preservatives, wetting agents, emulsifying agents, dispersing agents, preservatives or buffers, which may enhance the shelf life or effectiveness of the pharmaceutical composition. Compounds of the present invention may for instance be admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. Other examples of adjuvants are QS21, GM-CSF, SRL-172, histamine dihydrochloride, thymocartin, Tio-TEPA, monophosphoryl-lipid A/microbacteria compositions, alum, incomplete Freund's adjuvant, montanide ISA, ribi adjuvant system, TiterMax adjuvant, syntex adjuvant formulations, immune-stimulating complexes (ISCOMs), gerbu adjuvant, CpG oligodeoxynucleotides, lipopolysaccharide, and polyinosinic polycytidylic acid.

A (pharmaceutical) composition comprising a CD19×CD3 bispecific antibody is, for example, described in WO 2007/068354.

Prevention of presence of microorganisms may be ensured both by sterilization procedures and by the inclusion of various antibacterial and antifungal agents, for example, paraben, chlorobutanol, phenol, sorbic acid, and the like. In addition, prolonged absorption of the injectable pharmaceutical form may be brought about by the inclusion of agents which delay absorption, such as aluminum monostearate and gelatin. The pharmaceutical compositions containing the antibodies comprising a compound of the present invention may also include a suitable salt therefore. Any suitable salt, such as an alkaline earth metal salt in any suitable form (e.g., a buffer salt), may be used in the stabilization of the compound of the present invention. Suitable salts typically include sodium chloride, sodium succinate, sodium sulfate, potassium chloride, magnesium chloride, magnesium sulfate, and calcium chloride. In one embodiment, an aluminum salt is used to stabilize a compound of the present invention in a pharmaceutical composition of the present invention, which aluminum salt also may serve as an adjuvant when such a composition is administered to a patient. The pharmaceutical compositions containing the antibodies may be in a variety of suitable forms. Such forms include, for example, liquid, semisolid and solid dosage forms, such as liquid solutions (e.g., injectable and infusible solutions), dispersions or suspensions, emulsions, microemulsions, gels, creams, granules, powders, tablets, pills, powders, liposomes, dendrimers and other nanoparticles (see for instance Baek et al., Methods Enzymol. 362, 240-9 (2003), Nigavekar et al., Pharm Res. 21(3), 476-83 (2004), microparticles, and suppositories.

A "pharmaceutically acceptable salt" refers to a salt that retains the desired biological activity of the parent compound and does not impart any undesired toxicological effects (see for instance Berge, S. M. et al., J. Pharm. Sci. 66, 1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous acids and the like, as well as from nontoxic organic acids, such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

It is envisaged that the pharmaceutical composition of the present invention is employed in co-therapy approaches, i.e. in co-administration with other medicaments or drugs, for example, other medicaments for treating malignant CD19 positive lymphocytes in a patient and/or any other therapeutic agent which might be beneficial in the context of the methods of the present invention. An example of a co-administered medicament or drug is a chemotherapeutic such as dexamethasone. However, as mentioned herein, though dexamethasone is also known to be a chemotherapeutic, it is preferably used in the context of the present invention as compound that aids in ameliorating and/or avoiding/preventing adverse effects such as, in particular, neurological effects as described elsewhere herein.

Administration "in combination with" one or more further therapeutic agents includes simultaneous (concurrent) and consecutive administration in any order.

"Treatment" is herein defined as the application or administration of a CD19×CD3 bispecific antibody to a patient, or application or administration of CD19×CD3 bispecific antibody to an isolated tissue or cell line from a patient, where the patient has DLBCL or is at a risk of developing DLBCL, a symptom of DLBCL, or a predisposition towards DLBCL, where the purpose is to cure, heal, alleviate, relieve, alter, remedy, ameliorate, improve, or affect DLBCL, the symptoms of DLBCL, or the predisposition towards DLBCL. By "treatment" is also intended the application or administration of a pharmaceutical composition comprising the CD19×CD3 bispecific antibody to a patient, or application or administration of a pharmaceutical composition comprising the CD19×CD3 bispecific antibody, to an isolated tissue or cell line from a patient, who has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease. The pharmaceutical composition applied in the present invention preferably comprises a "therapeutically effective amount" of a CD19×CD3 bispecific antibody.

A "therapeutically effective amount," or "effective amount," of a composition with respect to DLBCL interchangeably refers to, in one embodiment, an amount of the composition that delays, reduces, palliates, ameliorates, stabilizes, prevents and/or reverses one or more symptoms (e.g., clinical symptom, biochemical symptom, etc.) that are associated with DLBCL compared to in the absence of the composition. This includes using dosages and periods of time necessary, to achieve the desired therapeutic result. The term "delaying" symptoms refers to increasing the time period between exposure to the CD19×CD3 bispecific antibody and the onset of one or more symptoms as described herein. The term "eliminating" symptoms refers to 40, 50, 60, 70, 80, 90 or even 100% reduction of one or more symptoms as described herein. A therapeutically effective amount also includes one in which any toxic or detrimental effects of the composition are outweighed by therapeutically beneficial effects.

A "prophylactically effective amount" refers to an amount effective, at dosages and for periods of time necessary, to achieve a desired prophylactic result, since a prophylactic dose is used in subjects prior to or at an earlier stage of disease, the prophylactically effective amount may be less than the therapeutically effective amount. Specific dosages can be readily determined by clinical trials and depend, for example, on the route of administration, disease state, age, sex, and weight of the individual (e.g. milligrams of drug per kg body weight). A prophylaxis could, for example, be achieved by the application of a CD19×CD3 bispecific antibody as described herein when it is administered to a patient prior to stem cell therapy, preferably autologous stem cell therapy, in order to eliminate (deplete) malignant CD19 expressing cells. Dosages are further discussed below.

The exact dose will depend on the purpose of the treatment, and will be ascertainable by one skilled in the art using known techniques. As is known in the art and described above, adjustments for age, body weight, general health, sex, diet, drug interaction and the severity of the condition may be necessary, and will be ascertainable with routine experimentation by those skilled in the art. The therapeutic effect of the respective methods or method steps of the present invention is additionally detectable by all established methods and approaches which will indicate a therapeutic effect. It is, for example, envisaged that the therapeutic effect is detected by way of surgical resection or biopsy of an affected tissue/organ which is subsequently analyzed by way of immunohistochemical (IHC) or comparable immunological techniques. Alternatively it is also envisaged that the tumor markers in the serum of the patient (if present) are detected in order to diagnose whether the therapeutic approach is already effective or not. Additionally or alternatively it is also possible to evaluate the general appearance of the respective patient (fitness, well-being, decrease of tumor-mediated ailment etc.) which will also aid the skilled practitioner to evaluate whether a therapeutic effect is already there. The skilled person is aware of numerous other ways which will enable him or her to observe a therapeutic effect of the compounds of the present invention.

By "therapeutically or prophylactically effective dose" or "therapeutically or prophylactically effective amount" is also intended an amount of a CD19×CD3 bispecific antibody that, when administered brings about a positive therapeutic response with respect to treatment of a patient with a DLBCL or pre-malignant condition associated with CD19-expressing cells. Suitable dosages are described in more detail elsewhere herein.

Thus, it is generally preferred that a composition comprising a CD19×CD3 bispecific antibody brings about a positive therapeutic response with respect to treatment of a patient with a DLBCL or pre-malignant condition associated with CD19-expressing cells.

By "positive therapeutic response" with respect to DLBCL or a pre-malignant condition associated therewith is intended an improvement in DLBCL or a pre-malignant condition associated therewith in association with the therapeutic activity of the CD19×CD3 bispecific antibody, and/or an improvement in the symptoms associated with DLBCL or pre-malignant condition associated therewith. That is, an antiproliferative effect, the prevention of further tumor outgrowths, a reduction in tumor size, a reduction in the number of cancer cells, and/or a decrease in one or more symptoms associated with CD19-expressing cells can be observed. Thus, for example, a positive therapeutic response would refer to one or more of the following improvements in the disease: (1) a reduction in tumor size; (2) a reduction in the number of cancer (i.e., neoplastic) cells; (3) an increase in neoplastic cell death; (4) inhibition of neoplastic cell survival; (4) inhibition (i.e., slowing to some extent, preferably halting) of tumor growth; (5) inhibition (i.e., slowing to some extent, preferably halting) of cancer cell infiltration into peripheral organs; (6) inhibition (i.e., slowing to some extent, preferably halting) of tumor metastasis; (7) the prevention of further tumor outgrowths; (8) an increased patient survival rate; and (9) some extent of relief from one or more symptoms associated with DLBCL.

Positive therapeutic responses in any given malignancy can be determined by standardized response criteria specific to that malignancy. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation. In addition to these positive therapeutic responses, the patient undergoing therapy with the CD19×CD3 bispecific antibody may experience the beneficial effect of an improvement in the symptoms associated with the disease. Thus for DLBCL, the patient may experience a decrease in the so-called B symptoms as described herein, such as night sweats, fever, weight loss, and/or urticaria.

An improvement in the disease may be characterized as a complete response. By "complete response" is intended an absence of clinically detectable disease with normalization of any previously abnormal imaging studies such as radiographic studies. Such a response preferably persists for at least 4 to 8 weeks, sometimes 6 to 8 weeks or more than 8, 10, 12, 14, 16, 18 or 20 weeks or longer, following treatment according to the invention. Alternatively, an improvement in the disease may be categorized as being a partial response. By "partial response" is intended at least about a 50% decrease in all measurable tumor burden (i.e., the number of malignant cells present in the patient, or the measured bulk of tumor masses) in the absence of new lesions and persisting for 4 to 8 weeks or more than 8, 10, 12, 14, 16, 18 or 20 weeks or longer. A "complete response" does, however, not necessarily indicate that DLBCL has been cured, since a patient may relapse. However, if so, the patient can again be treated with a composition comprising a CD19×CD3 bispecific antibody as described herein. Detailed remission and response definitions for NHL patients are used according to Cheson et al., 1999, J. Clin. Oncol. April; 17(4):1244.

In some embodiments, the patient is pre-treated, advantageously with chemotherapy such as CHOP or DHAP, experimental chemotherapy and/or chemoimmunotherapy such as R-CHOP, R-DHAP, R-ICE, R-VIPE, R-Treo/Flud or has undergone autologous stem cell therapy (SCT).

By "pretreated" or "pretreatment" is intended the patient has received one or more other DLBCL therapies (i.e., been treated with at least one other DLBCL therapy) prior to receiving the composition comprising the CD19×CD3 bispecific antibody. "Pretreated" or "pretreatment" includes patients that have been treated with at least one other DLBCL therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the composition comprising the CD19×CD3 bispecific antibody. It is not necessary that the patient was a responder to pretreatment with the prior DLBCL. Thus, the patient that receives the composition comprising the CD19×CD3 bispecific antibody could have responded, or could have failed to respond (i.e. DLBCL was refractory), to pretreatment with the prior DLBCL therapy, or to one or more of the prior DLBCL therapies where pretreatment comprised multiple DLBCL therapies.

Moreover, in other embodiments the patient is treated according to the means and methods of the present invention before s/he undergoes SCT.

In some embodiments, the patient is refractory to chemotherapy treatment or experimental chemotherapy treatment and/or in relapse after treatment with chemotherapy or experimental chemotherapy treatments.

In some of the foregoing embodiments, the patient is resistant to standard chemotherapeutic or experimental chemotherapy treatments.

A "patient" is a human individual (or subject) who will be or is treated with a CD19×CD3 bispecific antibody. In accordance with the present invention, the patient is suspected/assumed to comprise or already comprises malignant CD19 positive lymphocytes (in particular B cells). In the latter case, said patient has already been diagnosed (preferably, as described herein above) to comprise such cells and, thus, DLBCL. These malignant CD19 positive lymphocytes (in particular B cells) are present in a patient developing and/or suffering from DLBCL. In accordance with the present invention a patient is thus in need of a treatment of malignant CD19 positive lymphocytes.

"Malignant" describes lymphocytes (in particular B cells) that contribute to a progressively worsening disease, in particular DLBCL. The term is most familiar as a description of cancer, here DLCBL. Malignant CD19 positive lymphocytes (in particular B cells) are not self-limited in their growth, are capable of invading into adjacent tissues, and may be capable of spreading to distant tissues (metastasizing). Malignant when used herein is synonymous with cancerous.

However, as "normal" (non-malignant) lymphocytes (in particular B cells) also express CD19, it is to be expected that the CD19×CD3 bispecific antibody also binds these normal lymphocytes (in particular B cells) and upon recruiting cytotoxic T cells (because of the second specificity of the bispecific CD19×CD13 antibody) depletes these normal B cells. Yet, it is expected that the population of these normal B cells is reconstituted in the absence of the CD19×CD3 bispecific antibody. It was observed by Leandro and co-workers that after their depletion by an anti-CD20 antibody, B cells were reconstituted in rheumatoid arthritis patients (Arthritis Rheum. 2006 February; 54(2):613-20). As CD20, likewise CD19 is expressed on almost all B cells, it can be expected that B cells upon depletion by the bispecific CD19×CD3 antibody are reconstituted, too.

The term "administering" in all of its grammatical forms means administration of a CD19×CD3 bispecific antibody (in the form of a pharmaceutical composition) either as the sole therapeutic agent or in combination with another therapeutic agent.

Accordingly, in the context of the present invention "administration of a CD19×CD3 bispecific antibody" or "administering a CD19×CD3 bispecific antibody" or any other grammatical form thereof means that the CD19×CD3 antibody is in the form of a composition, preferably a pharmaceutical composition, optionally comprising a pharmaceutically acceptable carrier. Accordingly, it is to be understood that a composition, preferably a pharmaceutical composition, comprising a CD19×CD3 bispecific antibody is administered to a human patient. When administered to a patient, preferably a therapeutically effective dose of a composition comprising a CD19×CD3 bispecific antibody is administered to a patient. Accordingly, the composition of the present invention preferably includes a "therapeutically effective amount" or a "prophylactically effective amount" of CD19×CD3 bispecific antibody.

Similarly, it is also preferred that the composition comprising a CD19×CD3 bispecific antibody has anti-tumor activity. By "anti-tumor activity" is intended a reduction in the rate of malignant CD19-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one CD19×CD3 bispecific antibody causes a physiological response that is beneficial with respect to treatment of disease states.

"Tumor", as used herein, refers to all neoplastic cell growth and proliferation of malignant CD19-expressing B-cells, and all pre-cancerous and cancerous B-cells and tissues that gives rise to DLBCL. A tumor leads to tumorous mass, in particular to tumorous mass of lymph node tissue and/or extranodal lymphoma caused by DLBCL. "Neoplastic," as used herein, refers to any form of dysregulated or unregulated cell growth resulting in abnormal tissue growth. Thus, "neoplastic cells" include malignant B-cells having dysregulated or unregulated cell growth.

The terms "cancer" and "cancerous" refer to or describe the physiological condition in a patient that is typically characterized by unregulated cell growth. In the context of the present invention the cancer is preferably DLBCL.

The tumorous mass of lymph node tissue and/or extranodal lymphoma caused by DLBCL is preferably characterized by tumours having a size of more than 10×10 mm, more preferably 15×15 mm and even more preferably of more than 20×20 mm or even larger. Likewise, if determined in three dimensions, the tumorous mass of lymph node tissue and/or extranodal lymphoma caused by DLBCL is preferably characterized by tumours having a size of more than 10×10×10 mm, more preferably 15×15×15 mm and even more preferably of more than 20×20×20 mm or even larger.

Lymph node tissue preferably includes lymph nodes (including lymph node regions and/or lymph structures) and spleen. Lymph node regions can be defined as an area of lymph nodes and the surrounding tissue. Examples include the cervical nodes in the neck, the axillary nodes in the armpit, the inguinal nodes in the groin, and/or the mediastinal nodes in the chest. Lymph structures can be defined as organs or structures that are part of the lymphatic system, such as the lymph nodes, spleen, and thymus gland.

Accordingly, in some of the foregoing embodiments, the patient has, inter alia, at least one, two, three, four, five or more enlarged lymph node(s).

"Extranodal lymphoma": lymphomas can be considered as extranodal when, after routine staging procedures, there is either no or only 'minor' nodal involvement along with a clinically 'dominant' extranodal component, to which primary treatment must often be directed. Preferably extranodal lymphoma includes central nervous system (CNS), cutaneous tissue, breast, lungs, liver, gastrointestinal tract, genitourinary tract, ocular tissue, bone marrow and/or bones.

The administration of a pharmaceutical composition referred to herein is preferably an intravenous administration. It may be continually (continuously) administered.

A continual administration refers to an administration which is essentially without interruption. "Essentially without interruption" includes a continual administration usually without an uninterrupted flow or spatial extension.

In a preferred embodiment, a first dose of the (pharmaceutical) composition is administered for a first period of time and consecutively a second dose of the composition is administered for a second period of time, wherein the second dose exceeds the first dose.

The term "exceeds" means that the second period of time is at least one day longer than the first period of time.

It must be understood that the dose or day ranges given herein are illustrated by increments of one, two, three, four or five. These ranges, however, in case of increments higher than one also encompass smaller increments, for example those exemplified by increments of one (10 to 30 includes for example 10, 11, 12, 13, 13 etc. up to 30), or still smaller increments, for example values after the decimal point.

In another preferred embodiment of the present invention, it is envisaged that said first period of time is at least 3 days long, whereby even longer periods of time of for example 8, 9, 10, 11, 12, 13 or 14 days are not excluded. "Longer" is thereby not limited to a (one) complete day as the lowest time unit, i.e. ¾ days, or fully hours are also conceivable. It is however preferred that the smallest time unit is one full day.

Accordingly, said first period of time exceeds 3 days. More preferably, it is envisaged that said first period of time is between 3 days and 10 days, with 7 days being particularly preferred.

As used herein, a time interval which is defined as "X to Y" equates with a time interval which is defined as "between X and Y". Both time intervals specifically include the upper limit and also the lower limit. This means that for example a time interval "3 to 10 days" or between "3 to 10 days" includes a period of time of one, two, three, four, five, six, seven and/or eight days.

The duration of the first period of time, the duration of the second period of time may be variable in view of, for example, the age, sex, body weight, etc. of the human patient.

Accordingly, in another preferred embodiment of the present invention, it is envisaged that said second period of time is at least 18 days long, whereby even longer periods of time of for example 19, 20, 25, 30, 35, 40, 45, 49, 50, 55, 60, 65, 60, 65, 70, 75, 80, 81, 82, 83, 84, 85, 86, 87, 88 or 90 days are not excluded. "Longer" is thereby not limited to a (one) complete day as the lowest time unit, i.e. ¾ days, or fully hours are also conceivable. It is however preferred that the smallest time unit is one full day.

Accordingly, said second period of time exceeds 18 days. More preferably, it is envisaged that said second period of time is between 18 days and 81 days, with 21 or 49 days being particularly preferred.

As used herein, a time interval which is defined as "X to Y" equates with a time interval which is defined as "between X and Y". Both time intervals specifically include the upper limit and also the lower limit. This means that for example a time interval "18 to 81 days" or between "18 to 81 days" includes a period of time of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 61, 62, 63 and/or 64 days.

In a more preferred embodiment of the present invention, said first period of time is between 3 days and 10 days, and said second period of time is between 18 and 81 days.

In an even more preferred embodiment, said first period of time is 7 days and said second period of time is 21 or 49 days.

Accordingly, in a further preferred embodiment of the methods/dosage regimens of the present invention, said first dose is between 1 and 15 µg/m$^2$/d, i.e. 1, 2, 3, 4, 5, 6, 7, 8, 9, 10, 11, 12, 13, 14, 15 µg/m$^2$/d. Particularly preferred is a dose of 5 or 15 µg/m$^2$/d.

As used herein, a dose interval which is defined as "between X and Y" equates with a dose interval which is defined as "X to Y". Both dose intervals specifically include the upper limit and also the lower limit. This means that for example a dose interval "between 1 and 15" or "1 to 15" includes a dose of 1, 2, 3, 4, 5, 6, 7, 8, 9, 10, 11, 12, 13, 14, 15 µg/m$^2$/d.

In a further preferred embodiment, the present invention encompasses the continuous administration of a flat dose of the antibody without escalation to a subsequent higher dose. For example, the present administration includes the administeration of 60 µg/m$^2$/24 h, 15 µg/m$^2$/24 h or 5 µg/m$^2$/24 h of a CD19×CD3 bispecific single chain antibody until the conclusion of a course of the treatment up to 8 weeks [56 days] and even longer if determined to be safe and effective. "d" denotes one day.

"m$^2$" denotes a square meter of a patient's body surface (BSA). The "normal" average BSA is generally taken to be about 1.73 m$^2$ for an adult, for a neonate it is about 0.25 m$^2$, for a 2 year old child it is about 0.5 m$^2$, for a 9 year old child it is about 1.07 m$^2$, for a 10 year old child it is about 1.14 m$^2$, for a 12-13 year old child it is about 1.33 m², for men it is about 1.9 m² and for women it is about 1.6 m².

However, the BSA can also be calculated more precisely by one of the following formulas (each of these formulas can be applied when calculating the BSA):

The Mosteller formula (Mosteller, N Engl J Med 1987 Oct. 22; 317(17): 1098):

$$BSA\ (m^2) = ([Height(cm) \times Weight(kg)]/3600)^{1/2}$$ or in inches and pounds:

$$BSA(m^2) = ([Height(in) \times Weight(lbs)]/3131)^{1/2}$$

The DuBois formula (DuBois, Arch Int Med 1916 17:863-871):

$$BSA(m^2) = 0.007184 \times Height(cm)^{0.725} \times Weight(kg)^{0.425}$$

The Haycock formula (Haycock, The Journal of Pediatrics 1978 93:1: 62-66):

$$BSA(m^2) = 0.024265 \times Height(cm)^{0.3964} \times Weight(kg)^{0.5378}$$

The Gehan formula (Gehan, Cancer Chemother Rep 1970 54:225-35):

$$BSA(m^2) = 0.0235 \times Height(cm)^{0.42246} \times Weight(kg)^{0.51456}$$

The Boyd formula (Boyd, University of Minnesota Press, 1935)

$$BSA(m^2) = 0.0003207 \times Height(cm)^{0.3} \times Weight(grams)^{(0.7285 - (0.0188 \times \log 10(grams))}$$

It is generally preferred that each of the doses disclosed herein can be converted from amount (in µg)/m²/d into µg/d by multiplying the respective dose with the factor 1.9. Accordingly, each of the doses disclosed herein can be applied in the methods and uses by multiplying it with the factor 1.9. For example, a dose of 5 µg/m²/d is converted into 9.5 µg/d, a dose of 15 µg/m² is converted into 28.5 µg/m²/and a dose of 60 µg/m²/is converted into 114 µg/m². It is preferred that a decimal digit that results from the multiplication is either rounded up or rounded down, respectively, to a whole number. For example, a dose of 9.5 µg/d can be rounded down to 9 µg/d and a dose of 28.5 µg/m² can be rounded down to 28 µg/d. Likewise, a dose of 9.5 µg/d can be rounded up to 10 µg/d and a dose of 28.5 µg/m² can be rounded up to 29 µg/d.

The term "µg" includes "µg of the CD19×CD3 bispecific antibody preparation". It is preferred that not more than 10% of said CD19×CD3 bispecific antibody preparation is incorrectly folded. It follows that in a preferred embodiment, 90%, 91%, 92%, 93%, 94% or even 95% of the CD19×CD3 bispecific antibody is correctly folded, see, for example, WO 2005/052004 It is also conceivable that the antibody preparation may optionally comprise further ingredients, for example a lyoprotectant, a surfactant, a filler, a binder, and/or bulking agent etc. The amount of such further ingredients is, preferably, not included in the term "µg" as used in the context of the "dose" and/or methods (dosage regimens) of the present invention.

A dose of, for example, 1 µg/m²/d means that 1 µg of the CD19×CD3 bispecific antibody is administered evenly or continuously across one day per square meter body surface of the respective patient. "Continuously across one day" refers to an infusion which is allowed to proceed permanently without interruption.

It is a preferred embodiment that said second dose is between 15 and 60 µg/m²/d, i.e. 15, 20, 25, 30, 35, 40, 45, 50, 55 and 60 µg/m²/d. Particularly preferred is a dose of 60 µg/m²/d. Said second dose is thus therapeutically active.

In a preferred embodiment, said first dose is between 5 and 15 µg/m²/d and said second dose is between 15 and 60 µg/m²/d.

As used herein, a dose interval which is defined as "between X and Y" equates with a dose interval which is defined as "X to Y". Both dose intervals specifically include the upper limit and also the lower limit. This means that for example a dose interval "between 15 and 60" or "15 to 60" includes a dose of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 and/or 60 µg/m²/d.

It must be understood that the ranges given herein are illustrated by increments of five. These ranges, however, also encompass smaller increments, for example those exemplified by increments of one (10 to 30 includes for example 10, 11, 12, 13, 13 etc. up to 30), or still smaller increments, for example values after the decimal point.

Preferably, not included in the uses and methods of the present invention that apply a CD19×CD3 bispecific antibody are the following administration schemes:

(i) 5 µg/m² of the bispecific antibody for one day followed by administration of 15 µg/m² as daily dose for the remaining period (second and each further consecutive day); and/or (ii) 15 µg/m² of the bispecific antibody for one day followed by administration of 45 µg/m² as daily dose for the remaining period (second and each further consecutive day); and/or (iii) 5 µg/m² of the bispecific antibody for one day followed by administration of 15 µg/m² for one day, followed by administration of 45 µg/m² as daily dose for the remaining period (third and each further consecutive day); and/or (iv) less than 10-80 µg/m² of the bispecific antibody for one day followed by administration of a dose of 10-80 µg/m² (second and each further consecutive day); and/or (v) less than 10-80 µg/m² of the bispecific antibody for one day followed by administration of a dose of less 10-80 µg/m² for one day, followed by administration of a dose of less 10-80 µg/m² (third and each further consecutive day).

In another preferred embodiment of the present application, a third dose of said antibody is administered for a third period of time after administering a first and second dose for a first and second period of time. Accordingly, the present invention provides a three-stage (three-step) administration scheme (dosage regimen) to be applied in the uses and methods described herein.

The administration of said third dose is preferably intravenously. It can advantageously be administered continuously.

In a preferred embodiment of the present invention, said third period of time exceeds said first and second period of time. The term "exceeds" means that the third period of time is at least one day longer than the first and second period of time.

Likewise the duration of the first and second period of time, the duration of the third period of time may be variable in view of, for example, the age, sex, body weight, etc. of the human patient.

In the three-stage administration regimen of the present invention, it is envisaged that said first period of time is at least 3 days long, whereby even longer periods of time of for example 8, 9, 10, 11, 12, 13 or 14 days are not excluded. "Longer" is thereby not limited to a (one) complete day as the lowest time unit, i.e. ¾ days, or fully hours are also conceivable. It is however preferred that the smallest time unit is one full day.

Accordingly, said first period of time exceeds 3 days. More preferably, it is envisaged that said first period of time is between 3 days and 10 days, with 7 days being particularly preferred.

As used herein, a time interval which is defined as "X to Y" equates with a time interval which is defined as "between X and Y". Both time intervals specifically include the upper limit and also the lower limit. This means that for example a time interval "3 to 10 days" or between "3 to 10 days" includes a period of time of one, two, three, four, five, six, seven and/or eight days.

In the three-stage administration scheme of the present invention, it is envisaged that said second period of time is at least 3 days long, whereby even longer periods of time of for example 8, 9, 10, 11, 12, 13 or 14 days are not excluded. "Longer" is thereby not limited to a (one) complete day as the lowest time unit, i.e. ¾ days, or fully hours are also conceivable. It is however preferred that the smallest time unit is one full day. Accordingly, said first period of time exceeds 3 days. More preferably, it is envisaged that said first period of time is between 3 days and 10 days, with 7 days being particularly preferred.

As used herein, a time interval which is defined as "X to Y" equates with a time interval which is defined as "between X and Y". Both time intervals specifically include the upper limit and also the lower limit. This means that for example a time interval "3 to 10 days" or between "3 to 10 days" includes a period of time of one, two, three, four, five, six, seven and/or eight days.

In the three-stage administration scheme of the present invention, it is envisaged that said third period of time is at least 8 days long, whereby even longer periods of time of for example 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 61, 62, 63, 64, 65, 66, 67, 68, 69, 70 and/or 71 days are not excluded. "Longer" is thereby not limited to a (one) complete day as the lowest time unit, i.e. ½ days, or fully hours are also conceivable. It is however preferred that the smallest time unit is one full day. Accordingly, said first period of time exceeds 8 days. More preferably, it is envisaged that said first period of time is between 8 days and 78 days, with 14 or 42 days being particularly preferred.

As used herein, a time interval which is defined as "X to Y" equates with a time interval which is defined as "between X and Y". Both time intervals specifically include the upper limit and also the lower limit. This means that for example a time interval "18 to 78 days" or between "18 to 78 days" includes a period of time of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 61, 62 63, 64, 65, 66, 67, 68, 69, 70 and/or 71 days.

In a more preferred embodiment of the three-stage administration scheme of the present invention, said first period of time is between 3 days and 10 days, and said second period of time is between 3 days and 10 days, and said third period of time is between 8 days and 78 days.

In an even more preferred embodiment, said first period of time is 7 days, said second period of time is 7 days, and said third period of time is 14 or 42 days.

In a preferred embodiment of the three-stage administration scheme of the present invention, said third dose exceeds said first and second dose. Said second and third dose are preferably therapeutically active. Of note, said second dose exceeds said first dose.

Accordingly, in a further preferred embodiment of the three-stage administration scheme of the present invention, said first dose is between 1 and 15 $\mu g/m^2/d$, preferably between 5 and 15 $\mu g/m^2/d$, i.e. 1, 2, 3, 4, 5, 6, 7, 8, 9, 10, 11, 12, 13, 14, 15 $\mu g/m^2/d$. Particularly preferred is a dose of 5 or 10 $\mu g/m^2/d$.

In a further preferred embodiment of the three-stage administration scheme of the present invention, said second dose is between 1 and 15 $\mu g/m^2/d$, preferably between 5 and 15 $\mu g/m^2/d$, i.e. 1, 2, 3, 4, 5, 6, 7, 8, 9, 10, 11, 12, 13, 14, 15 $\mu g/m^2/d$. Particularly preferred is a dose of 15 $\mu g/m^2/d$.

As used herein, a dose interval which is defined as "between X and Y" equates with a dose interval which is defined as "X to Y". Both dose intervals specifically include the upper limit and also the lower limit. This means that for example a dose interval "between 1 and 15" or "1 to 15" includes a dose of 1, 2, 3, 4, 5, 6, 7, 8, 9, 10, 11, 12, 13, 14, 15 $\mu g/m^2/d$.

In a further preferred embodiment of the three-stage administration scheme of the present invention, said third dose is between 15 and 120 $\mu g/m^2/d$, more preferably between 15 and 90 $\mu g/m^2/d$, i.e. 15, 20, 25, 30, 35, 40, 45, 50, 55, 60, 65, 70, 75, 80, 85 and 90 $\mu g/m^2/d$, even more preferably said third dose is between 15 and 60 $\mu g/m^2/d$, even yet more preferably between 20 and 60 $\mu g/m^2/d$, i.e. 15, 20, 25, 30, 35, 40, 45, 50, 55 and 60 $\mu g/m^2/d$. Particularly preferred is a dose of 60 $\mu g/m^2/d$ or 90 $\mu g/m^2/d$.

In a preferred embodiment of the three-stage administration scheme of the present invention, said first dose is between 1 and 15 $\mu g/m^2/d$, said second dose is between 1 and 15 $\mu g/m^2/d$, and said third dose is between 15 and 60 $\mu g/m^2/d$ or 15 and 90 $\mu g/m^2/d$ or 15 and 120 $\mu g/m^2/d$.

Particularly preferred, said first dose is 5 $\mu g/m^2/d$, said second dose is 15 $\mu g/m^2/d$, and said third dose is 60 or 90 $\mu g/m^2/d$ As used herein, a dose interval which is defined as "between X and Y" equates with a dose interval which is defined as "X to Y". Both dose intervals specifically include the upper limit and also the lower limit. This means that for example a dose interval "between 15 and 60" or "15 to 60" includes a dose of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 and/or 60 $\mu g/m^2/d$. Similarly, this means that for example a dose interval "between 15 and 90" or "15 to 90" includes a dose of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 86, 87, 88, 89 or 90 $\mu g/m^2/d$.

In a preferred embodiment, dexamethasone is administered together with the CD19×CD3 bispecific antibody. Specifically, this administration includes one or more pretreatment step(s) with dexamethasone before the administration of the first dose of the CD19×CD3 bispecific single chain antibody. In a three-stage administration scheme, dexamethasone is administered prior to first dose and prior to the increase to the second and/or third doses of the CD19×CD3 bispecific single chain antibody. Further, dexamethasone is optionally administered for an additional 1 or 2 days after the first dose and after each successive dose increase. As mentioned above, it was observed that dexamethasone treatment reduces or alleviates (adverse) neurological effects/reactions such as confusion, ataxia, disorientation, dysphasia, aphasia, speech impairment, cerebellar symptoms, tremor, apraxia, seizure, grand mal convulsion, palsy and/or balance disorder.

More specifically, in a three-stage administration scheme, dexamethasone is administered in the range of between 6 and 48 hours before the administration of the first dose of the CD19×CD3 bispecific antibody, more preferably between 6 and 12 hours, and more preferably 12 hours, before the first dose administration. Then approximately 1 hour before (range 15 min-2 h including 30 min, 45 min, 60 min, 75 min, 90 min) the first dose of the antibody is administered, a dose of dexamethasone is again administered to the patient. Then dexamethasone is administered 1 or more days, preferably 2 to 3 days, after the first dose of the antibody, preferably on the two days after the first antibody administration and administered 2 or more days after each dose increase, preferably on the two days after the administration of the dose increase of the antibody. Each of the dexamethasone doses is preferably between 6 and 40 mg, and preferably at approximately 20 or 24 mg per dose.

The time range between 6 and 48 hours includes the administration of the dexamethasone dose and means that the times prior to the first administration of the antibody are 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 and 48 hours. Similarly, the preferred time range between 6 and 12 hours includes the administration of the dexamethasone dose prior to the first administration of the antibody and includes 6, 7, 8, 9, 10, 11 and 12 hours, In a further embodiment, dexamethasone is administered for a period of two, three, four or five days during which the dose of the CD19×CD3 bispecific antibody is increased. For example, dexamethasone is administered at a first point of time in a dose of 6 to 40 mg or 6 to 48 mg, preferably 20, 24, 28, 32, 36, 40, 44 or 48 mg, with 20 or 24 mg being preferred, at a second point of time in a dose of preferably 8, 12, 16, 20, or 24 mg, with 16 mg being preferred and/or at a third point of time in a dose of preferably 2, 4, 6, 8, 10 or 12 mg, with 8 mg being preferred. It may also be administered at a fourth point of time or fourth and fifth point of time in a dose of preferably 2, 4, 6, 8, 10 or 12 mg, with 8 mg being preferred.

In a further embodiment, when dexamethasone is administered during the increase of the doses of the CD19×CD3 bispecific antibody between the first and second period or between the second and third period of time, respectively, as described herein, it is administered at day n−3, n−2, n−1, n, n+1, n+2 and/or n+3, wherein n is the last day of the first or second period of time, respectively, and wherein the maximum amount of days during day n−3 and n+3 is 3, 4 or 5 days, with 3 or 4 days being preferred. For example, dexamethasone may be administered during day n−3 and n+1, i.e at 5 days, or during day n−3 and n, i.e. at 4 days, or during day n−2 and day n+1, i.e. at 4 days or during day n−1 and n+1, i.e. at 3 days.

Accordingly, if dexamethasone is administered for 3, 4 or 5 days, it is envisaged that the above described administration scheme is preferably applied:
- at a first point of time in a dose of preferably 20, 24, 28, 32, 36, 40, 44 or 48 μg, with 24 μg being preferred (the same dose can be administered, but in mg instead of μg),
- at a second point of time in a dose of preferably 8, 12, 16, 20, or 24 μg, with 16 μg being preferred (the same dose can be administered, but in mg instead of μg),
- at a third point of time in a dose of preferably 2, 4, 6, 8, 10 or 12 μg, with 8 μg being preferred (the same dose can be administered, but in mg instead of μg),
- at a fourth point of time in a dose of preferably 2, 4, 6, 8, 10 or 12 μg, with 8 μg being preferred (the same dose can be administered, but in mg instead of μg), and/or
- at a fifth point of time in a dose of preferably 2, 4, 6, 8, 10 or 12 μg, with 8 μg being preferred (the same dose can be administered, but in mg instead of μg).

Alternatively, the dose of dexamethasone, can be the same [6-40 mg] at each administration, and preferably at 20 or 24 mg per dose.

It is also preferably envisaged that dexamethasone is administered on any day during the first, second and/or third period of time when the CD19×CD3 bispecific antibody is administered if neurological effects are observed.

An alternative embodiment of the present invention is to administer a flat or constant dose of the antibody without escalation to a subsequent higher dose as discussed above. For example, the present administration includes the administration of 5 μg/m$^2$/24 h, 15 μg/m$^2$/24 h or 60 μg/m$^2$/24 h of a CD19×CD3 bispecific single chain antibody until the conclusion of a course of the treatment up to 8 weeks [56 days] and even longer if determined to be safe and effective. In this embodiment, dexamethasone is administered in the range of 6 to 48 hours, preferably 6 to 12 hours, and more preferably 6 or 12 hours, and again no later than 1 hour (range 15 min-2 h including 30 min, 45 min, 60 min, 75 min, 90 min) before the administration of the first dose of the antibody. Dexamethasone is preferably administered for 1 or more days, preferably 2-3 days, after the administration of the antibody and if neurological effects are observed.

Though it is known that dexamethasone reduces the activity of immune cells including T-cells (CD4$^+$ and CD8$^+$ T-cells), since it is a known immunosuppressant, and it could thus have been expected that the CD19×CD3 bispecific antibody might not engage potent (active) T-cells, the present inventors observed the opposite. Indeed, the T-cells engaged by the CD19×CD3 bispecific antibody were apparently potent, since an outstanding reduction of tumor mass was observed in the clinical trials with DLBCL patients (see the appended Examples).

In a further aspect, the present invention relates to a pharmaceutical kit for treating tumor mass of lymph node tissue and/or extranodal lymphoma caused by diffuse large B cell lymphoma (DLBCL) in a patient comprising a composition of any one of the preceding claims and optionally means for instructions (instruction sheet).

In a still further aspect, the present invention relates to a (pharmaceutical) kit or pharmaceutical package comprising the first dose and the second dose as defined herein.

In another aspect, the present invention relates to a (pharmaceutical) kit or pharmaceutical package comprising the first dose and the second dose as defined herein as well as the third dose as defined in the context of the three-stage dosage regimen/method.

In yet another aspect, the (pharmaceutical) kit or pharmaceutical package comprises all three doses as defined herein in the context of the three-stage dosage regimen/method, i.e., the first, the second and the third dose.

Said first, second and third dose are thereby packaged together in one sealed pharmaceutical package or kit. It will be understood that the "first dose", the "second dose" and the "third dose" encompasses in this regard the respective number of single doses which will be used for a given period of time (either the first or the second period of time). This means for example that the "first dose" or "second dose" which is comprised in the pharmaceutical package or kit of the present invention comprises, for example, 7 daily doses which are separated. The number of packaged daily doses thereby reflects the intended period of time (X daily doses if said period of time is X days, Y daily doses if the period of time is Y days and so on). In these embodiments, the (pharmaceutical) kit or pharmaceutical package comprises the daily dosages in separate containers, in a single package.

Alternatively, it is also envisaged that the intended first dose and/or second dose and/or third dose is not separated into the respective number of daily doses but is contained, either in toto or in part, in one single container (for example an infusion bag), which comprises the required dose for either the first and/or the second period of time either in part (for example for 1 to 3 days) or in toto (i.e. for the first or second period of time). This means that one single container comprises for example 7 daily doses for the "first dose" which is to be used during the first period of time etc.

It will be understood that the (pharmaceutical) kit or pharmaceutical package of the present invention may also comprises more or less daily doses as required for the respective period of time (either separated or not). Alternatively, the (pharmaceutical) kit or pharmaceutical package is prepared such that it contains the required number of daily doses (either separated or not) for the first and second period of time as defined herein, i.e. the "first dose", the "second dose" and the "third dose" in one single package. Such a package is ideally sufficient for one complete treatment of a patient (including the first and the second period of time). Parts of the kit and package of the invention can be packaged individually in vials or bottles or in combination in containers or multicontainer units. The manufacture of the kits follows preferably standard procedures which are known to the person skilled in the art.

The present invention relates in a further aspect to a pharmaceutical package or kit as described hereinbefore and written instructions for the sequential use thereof in accordance with the methods of the present invention. Said pharmaceutical package or kit may further comprise a label or imprint indicating that the contents can be used for treating malignant CD19 positive lymphocytes present in lymphoma or leukemia in a human patient; or for ameliorating or preventing an adverse effect mediated by the administration of a CD19× CD3 bispecific antibody to a patient.

It is also envisaged that the pharmaceutical package or kit of the present invention, further comprises means to administer the first and/or the second dose and/or third dose to a patient and/or buffers, vials, teflon bags or infusion bags which are normally used for the infusion of therapeutic agents. "Means" thereby includes one or more article(s) selected from the group consisting of a syringe, a hypodermic needle, a cannula, a catheter, an infusion bag for intravenous administration, intravenous vehicles, vials, buffers, stabilizers, written instructions which aid the skilled person in the preparation of the respective doses and infusions of the invention etc.

It is also envisaged that the pharmaceutical package or kit of the present invention further comprises a chemotherapeutic agent.

In a further aspect, the present invention provides for a pharmaceutical package or kit, wherein said first and/or said second dose is arranged such, that it is suitable for (prepared for) administration of a dosage regimen in accordance with a method of any one of the preceding claims.

EXAMPLES

Various aspects and embodiments of the present invention will now be described in more detail by way of example only. It will be appreciated that modification of detail may be made without departing from the scope of the invention. Of note, all patients declared their consent to participate in the clinical trials.

Abbreviations
Staging of patients is done in accordance with Cheson et al. (2007), J. Clin. Oncol. 25(5):579-586

CR: complete remission
CRu: complete remission (unconfirmed)
DLT: dose limiting toxicity
EOS: end of study
LDH: lactate dehydrogenase
PD: progressive disease
PR: partial remission
SAE. Severe adverse effect
SCT: stem cell therapy
SD: stable disease
SPD: sum of diameter Example 1

Patient 109-033
Female, 42 y, DLBCL w. abdominal bulk
Stage: IVBE
B:T cell ratio: 0:141 (low
Prior Treatments:
  1. 6× R-CHOP 05/09-08/09
  2. 2× R-DHAP 10/09-11/09
  3. 1× R-ICE 12/09
Date of prior treatment: 12/09
Date of treatment start: 8.3.2010
Major Involvement:
  Abdominal Bulk 12×10×11 cm
a CT of April 7: tumor progress with abdominal bulk
  increasing from 12×10×11 cm to 16×15×12 cm
  additional infiltration of spleen and right kidney pole with parallel LDH increase
  Treatment stop
Treatment duration: 29+3d
Completed 60 µg/m$^2$/d without neurological adverse event
SAE: Lymphopenia
DLT: No Example 2

Patient 153-001
Male, 47 y, DLBCL
Stage: IVA
B:T cell ratio: 0:524 (low)
First diagnosis: 09/2009
Prior treatments:
  1. 6× R-CHOP
  2. 2× R-VIPE
  3. Status after abdominal debulking surgery
Dates of last previous treatment: 09/09-12/09
Treatment start: 29.3.2010
Major Involvement:
  Small Lesion 2.3×1.7 cm bladder region
No neurological adverse event.
CT after 4 wks: borderline SD
CT after 6 wks (additional): significant reduction compared to CT after 4 wks.
CT after 8 wks: PR with SPD −64,9
DLT: No
Retreatment started 12.7.2010
LowBT: 0:291
Planned CT: August 1

Example 3

Patient 109-034
Male, 40 y, DLBCL,
Stage II NE
B:T cell ratio: 0:501 (low)
First diagnosis: 06/07

Prior treatments:
 1. 8× R-CHOEP 06-10/07
 2. 2×DHAP 05-06/09
 3. 1×R-ICE 07/09
 4. R-Treo/Flud 08/09
 5. Autologous SCT 09/09
Data of last prior treatment: 09/09
Treatment start: 19.4.2010
Major Involvement:
 Abdominal 5.1×2.2 cm and 4.8×2.2 cm
Treatment start 19.4.
No neurological adverse event
SAE: Neutropenia
CT after 4 wks: SD/PD? (SPD increase of 31.1%)
 Still to be confirmed by reference radiologist
 Controversial gastric involvement; to be clarified
Treatment ongoing because of clinical benefit
CT after 8 weeks: PD +43.4%
DLT: No Example 4

Patient 109-035 (1 of 3)
Female, 67 y, ELBCL
Stage IIB
B:T cell ratio: 0:1808
First diagnosis: 09/06
Prior treatments:
 1. 6× R-CHC1P 09/06-04/07
  +2× Rituximab as consolidation
 2. 2× R-DHAP 01/09-08/09
 3. Zevalin BEAM 10/09
 4. Autologous SCT 11/09
Date of last treatment: 11/09
Treatment Start: 26.04.2010
Major Involvement:
 1. Right mamma
 2. Left inguinal
 3. Left lower leg
On d2 grade 2 CNS event (CTCAE Grade 2)
 primarily apraxia, only mild speech impairment,
  stop of treatment
12 h after stop neurological symptoms completely resolved
 MRT unremarkable, FACS-analysis of CSF not possible
  Attempt to stain for CD19 on fixed CSF samples not
   successful
Patient received CSF prophylaxis
 Viable B cells in CSF not likely to cause complication
Patient received other treatment meanwhile
Efficacy: N/A
DLT: No Example 5 (1 of 3)

Patient 135-001
Mate, 52 y, DLBCL
Stage: IVA
B:T cell ratio: 0:565 (tow)
First diagnosis: 1986 as FL
⇒ Transformation first diagnosis DLBCL 01/2008
Prior treatments:
 1. R-BEAM (BCNU, Etoposid, AraC and Melphalan
  reduced to 75%)
 2. Autologous SCT 10/09
Date of last prior treatment: 10/09
Treatment start: 10.5.2010

Major Involvement:
 infradiaphragmal
At 5 ug tremor and apraxia (difficulty writing) which
 resolved under steroid therapy.
Escalation to 15 ug on May, 17th and 60 ug on May, 24th
 No CNS complication
4 days after escalation (20:00 hrs) to 60 ug
 CNS complication with aphasia and disorientation
 Treatment stop (Thursday night)
 Event resolved within 24 hrs completely and no findings
  in EEG and MRT; patient was discharged from hospital on Saturday
 On Saturday afternoon: pseudo-hallucinations ("seeing faces")
Pseudo-hallucinations started to improve on June 2nd.
June 9: complete resolution (d12 of occurrence)
CT: PR?
DLT: yes
EOS: 28.6.10

Example 6

Patient 109-038 (1 of 3)
Female, 65 y, DLBCL
Initial Stage: IE
B:T cell ratio: high:576:863
First diagnosis: 1997
Prior treatments:
 1. 6×CHOP
 2. 2× R-DHAP
 3. 1× R-Dexa-Beam
 4. High Dose Beam w. autologous SCT
Date of last prior treatment: 09/05
Treatment start: 7.6 2010
Major Involvement:
 1. right mamma
 2. right axillary, left supradaviculary
 3. retroperitoneal and abdominal
Treatment start June, 7
 No neurological adverse event at 5 ug
Dose increase to 15 ug June 14
 No neurological adverse event
Dose increase to 60 ug June 21
 Mild neurological event resolved under steroid treatment
DLT: No
4W CT: CRu
Tm ongoing, SW CT planned August 4
4 W CT: -left supraclaviculary: 20×13 mm⇒ 12×10 mm
 17×13 mm⇒ 11×7 mm
 11×11 mm⇒ 9×7 mm
retroperitoneal: 38×19 mm⇒ 20×9 mm
paraaortal 40×24 mm⇒ 20×11 mm
 63×47 mm⇒ 45×26 mm
 48×45 mm⇒ not clearly identifiable Example 7

Summary DLBCL Patients Treated with 5/15/60 µg/m²/24 h

| Pat No. | Entity | St | Size of lesion | 60 µg | DLT | Response | CNS Event |
|---|---|---|---|---|---|---|---|
| 109-033 | DLBCL | IVBE | Abd. bulk | Yes | No | PD | No |
| 153-001 | DLBCL | IVA | Stat. after debulk. | Yes | No | 8W: PR −64.9% Retreatment 12.7 | No |
| 109-034 | DLBCL | IINE | Bulk | Yes | No | 8W: PD +43.4% | No |
| 109-035 | DLBCL | IIB | large | No | No | N/A | D 2 at 5 grade 2 |
| 135-001 | DLBCL | IVA | Small, no bulk | Yes | Yes | PR: 4W: −59%? | At 5 and 60 Resolved d 12 |
| 109-038 | DLBCL | IE | Extranod. ri. Mam. + axilla | Yes | No | 4 W CT: CRu: −75% | Mild and re-occurring |

Example 8

MT103 (CD19×CD3 Bispecific Antibody)—Dexamethasone

Therapeutic Dexamethasone (Dex) is beneficial (getting neurological symptoms to disappear without necessity to stop treatment):
  109-038 high-risk patient with DLBCL on d15 (at 60 µg); worked against intention tremor
  Dex prophylaxis worked for low risk patient 135-002 with DLBCL, who had only slight tremor in week 2.

Example 9

Patient 135-001 with DLBCL received the antibody at 5 µg/m²/d for one week, at 15 µg/m²/d for the $2^{nd}$ week, and 60 µg/m²/d for 4 more days. The patient received dexamethasone in order to treat tremor at 5 µg/m²/d on day 3 (3×8 mg) and continued to receive dexamethasone in decreasing dose over less than a week. There were no neurological events after escalation to 15 ug, which could be explained by a prophylactic effect of dexamethasone. However, on day 4 after step to 60 ug/m²/d the patient had to stop due to neurological adverse events which occurred too fast to intervene with dexamethasone.

Example 10

Patient 109-038 with DLBCL received the antibody at 5 µg/m²/d for one week, at 15 µg/m²/d for the $2^{nd}$ week, and 60 µg/m²/d for the remaining 6 weeks of treatment. On day 15 the patient developed intention tremor which resolved after dexamethasone (3×8 mg i.v. was given while continuing the antibody treatment).

Example 11

Patient 135-002 with DLBCL received the antiody at 5 µg/m²/d for one week, at 15 µg/m²/d for the $2^{nd}$ week, and 60 µg/m²/d for the remaining 2 weeks and in addition received dexamethasone prophylaxis (dose: 3×8 mg on the day of start of antibody treatment and on days of dose escalation steps). The patient did not have to discontinue treatment with antibody due to neurological/psychiatric adverse events.

Example 12

A Phase I clinical trial was performed in patients with various B-NHL including DLBCL to evaluate the CD19× CD3 bispecific antibody construct in DLBCL patients. Patients were treated for 4-8-weeks by continuous i.v. administration of the antibody with the following step-wise dosing regimen: first week at 5 µg/m²/d, second week at 15 µg/m²/d and for the remaining treatment period at 60 µg/m²/d.

Two cohorts each with 6 DLBCL patients were enrolled. The two cohorts solely differed by the dose and schedule of the glucocorticoid medication administered at the beginning of the antibody infusion for mitigation of adverse events.

Out of the twelve patients, 5 were male and 7 female. The median age was 57 years (range from 24 to 78 years). Patients had received a median of 4 prior regimens (range from 2-6). All patients had been exposed to rituximab. Eight of the 12 patients had undergone ASCT. International prognostic index (IPI) at screening ranged from 1 to 3 with a median of 2. In the first cohort 100 mg prednisolone was administered 1 hour prior to start; and in the second cohort patients received dexamethasone (3×8 mg) on days 1, 2, and 3. Before treatment start in the second cohort 20 mg dexamethasone was administered at 12 hours and 1 hour prior to the administration of a CD19×CD3 bispecific antibody construct.

Although just one DLT (reversible CNS event grade 3) occurred in the prednisolone DLBCL cohort and, thus, the cohort is considered safe, a further DLBCL cohort applying prophylactic dexamethasone (3×8 mg at start of infusion or dose increase and reduction to 3×6 mg or 3×4 mg on the following 2 days, respectively) was opened to optimize management of CNS events. In light of one of the first two patients having a DLT due to a reversible CNS adverse event, a modified "early dexamethasone" schedule (20 mg at −12 to −6 hours and −1 hour, at start of infusion or dose increase, and 3×8 mg during the following 2 days) was introduced to test if earlier and more intensive administration of dexamethasone may ameliorate CNS adverse events. No further DLTs were observed after this adjustment of the dexamethasone schedule. Thus, both the dexamethasone cohort as well as the "early dexamethasone administration" are considered safe. Among a total of 5 patients with DLBCL treated with the "early dexamethasone schedule" no DLT was observed. Therefore, it was concluded that additional administration of "early dexamethasone" is the safest way to administer blinatumomab to patients with DLBCL. Also for patients with "early dexamethasone" objective responses have been observed

The invention claimed is:

1. A method for treating a tumorous mass of lymph node tissue and/or extranodal lymphoma in a patient suffering from relapsed and/or refractory diffuse large B cell lymphoma (DLBCL), the method comprising the step of administering to the patient (i) a composition comprising an effective amount of a CD19×CD3 bispecific antibody in a step-wise application, whereby a first dose between 1 and 15 µg/m²/d of the CD19×CD3 bispecific antibody is administered daily for a first period of time from 3 to 10 days, a second dose between 1 and 15 μg/m²/d of the CD19×CD3 bispecific antibody is administered daily for a second period of time from 3 to 10 days, and a third dose between 15 and 60 μg/m²/d of the CD19×CD3 bispecific antibody is administered daily for a third period of time from 8 to 78 days; and (ii) a composition comprising an effective amount of a glucocorticoid to ameliorate adverse neurological effects of the antibody in the patient, whereby the glucocorticoid is administered prior to and after the CD19×CD3 bispecific antibody is administered.

2. The method of claim 1, wherein the tumorous mass is characterized by a tumor having a size of more than 10×10 mm.

3. The method of claim 1, wherein the lymph node tissue includes lymph nodes and/or spleen and the extranodal lymphoma includes central nervous system (CNS), cutaneous tissue, breast, lungs, liver, gastrointestinal tract, genitourinary tract, ocular tissue, bone marrow and/or bones.

4. The method of claim 1, wherein a first dose of the composition is administered for a first period of time and consecutively a second dose of the composition is administered for a second period of time, wherein the second dose exceeds the first dose.

5. The method of claim 1, wherein the third period of time exceeds the first period of time and the second period of time, and the second dose exceeds said first dose.

6. The method of claim 1, wherein the third dose exceeds the first dose and second dose.

7. The method of claim 1, wherein the first period of time exceeds 3 days, the second period of time exceeds 3 days and the third period of time exceeds 8 days.

8. The method of claim 1, wherein the first period of time is 7 days, the second period of time is 7 days and the third period of time is 14 or 42 days.

9. The method of claim 1, further comprising the step of administering a chemotherapeutic agent.

10. The method of claim 1, wherein the glucocorticoid is selected from the group consisting of cortisone, cortisol, cloprednol, prednisone, prednisolone, methylprednisolone, deflazacort, fluocortolone, triamcinolone, dexamethasone, betamethasone, flusticasonepropionate, and triamcinolonacetonide.

11. The method of claim 1, wherein the glucocorticoid is administered at a dose of between 6 to 40 mg prior to and after the administration of the CD19×CD3 bispecific antibody, and the antibody is administered at a first dose of 5 μg/m²/d, at a second dose of 15 μg/m²/d and at a third dose of 60 μg/m²/d.

12. The method of claim 1, wherein the CD19×CD3 bispecific single chain antibody construct comprises:
(a) a variable heavy chain anti-CD19 CDR1 comprising the amino acid sequence set forth in SEQ ID NO: 14, a variable heavy chain anti-CD19 CDR2 comprising the amino acid sequence set forth in SEQ ID NO: 15, and a variable heavy chain anti-CD 19 CDR3 comprising the amino acid sequence set forth in SEQ ID NO: 16; or
(b) a variable heavy chain anti-CD3 CDR1 comprising the amino acid sequence set forth in SEQ ID NO: 17, a variable heavy chain anti-CD3 CDR2 comprising the amino acid sequence set forth in SEQ ID NO: 180, and a variable heavy chain anti-CD3 CDR3 comprising the amino acid sequence set forth in SEQ ID NO: 19.

13. The method of claim 1, wherein the CD19×CD3 bispecific single chain antibody construct comprises:
(a) a variable heavy chain anti-CD3 CDR1 comprising the amino acid sequence set forth in SEQ ID NO: 11, a variable heavy chain anti-CD3 CDR2 comprising the amino acid sequence set forth in SEQ ID NO: 12, and a variable heavy chain anti-CD3 CDR3 comprising the amino acid sequence set forth in SEQ ID NO: 13;
(b) a variable light chain anti-CD3 CDR1 comprising the amino acid sequence set forth in SEQ ID NO: 14, a variable light chain anti-CD3 CDR2 comprising the amino acid sequence set forth in SEQ ID NO: 15, and a variable light chain anti-CD3 CDR3 comprising the amino acid sequence set forth in SEQ ID NO: 16;
(c) a variable heavy chain anti-CD19 CDR1 comprising the amino acid sequence set forth in SEQ ID NO: 17, a variable heavy chain anti-CD19 CDR2 comprising the amino acid sequence set forth in SEQ ID NO: 18, a variable heavy chain anti-CD19 CDR3 comprising the amino acid sequence set forth in SEQ ID NO: 19; or
(d) a variable light chain anti-CD19 CDR1 comprising the amino acid sequence set forth in SEQ ID NO: 20, a variable light chain anti-CD19 CDR2 comprising the amino acid sequence set forth in SEQ ID NO: 21, and a variable light chain anti-CD19CDR3 comprising the amino acid sequence set forth in SEQ ID NO: 22.

14. The method of claim 1, wherein the CD19×CD3 bispecific single chain antibody construct comprises:
(a) a variable heavy chain anti-CD3 CDR1 comprising the amino acid sequence set forth in SEQ ID NO: 11, a variable heavy chain anti-CD3 CDR2 comprising the amino acid sequence set forth in SEQ ID NO: 12, and a variable heavy chain anti-CD3 CDR3 comprising the amino acid sequence set forth in SEQ ID NO: 13; a variable light chain anti-CD3 CDR1 comprising the amino acid sequence set forth in SEQ ID NO: 14, a variable light chain anti-CD3 CDR2 comprising the amino acid sequence set forth in SEQ ID NO: 15, and a variable light chain anti-CD3 CDR3 comprising the amino acid sequence set forth in SEQ ID NO: 16; and/or
(b) a variable heavy chain anti-CD19 CDR1 comprising the amino acid sequence set forth in SEQ ID NO: 17, a variable heavy chain anti-CD19 CDR2 comprising the amino acid sequence set forth in SEQ ID NO: 18, a variable heavy chain anti-CD19 CDR3 comprising the amino acid sequence set forth in SEQ ID NO: 19; a variable light chain anti-CD19 CDR1 comprising the amino acid sequence set forth in SEQ ID NO: 20, a variable light chain anti-CD 19 CDR2 comprising the amino acid sequence set forth in SEQ ID NO: 21, and a variable light chain anti-CD19 CDR3 comprising the amino acid sequence set forth in SEQ ID NO: 22.

15. The method of claim 1, wherein the CD19×CD3 bispecific single chain antibody construct comprises:
(a) a variable heavy chain anti-CD19 amino acid sequence set forth in SEQ ID NO: 3;
(b) a variable light chain anti-CD19 amino acid sequence set forth in SEQ ID NO: 5;
(c) a variable heavy chain anti-CD3 amino acid sequence set forth in SEQ ID NO: 7; or (d) a variable light chain anti-CD3 amino acid sequence set forth in SEQ ID NO: 9.

16. The method of claim 1, wherein the CD19×CD3 bispecific single chain antibody construct comprises a variable heavy chain anti-CD19 amino acid sequence set forth in SEQ ID NO: 3 and a variable light chain anti-CD19 amino acid sequence set forth in SEQ ID NO: 5.

17. The method of claim 1, wherein the CD19×CD3 bispecific single chain antibody construct comprises a variable heavy chain anti-CD3 amino acid sequence set forth in SEQ ID NO: 7 and a variable light chain anti-CD3 amino acid sequence set forth in SEQ ID NO: 9.

18. The method of claim 1, wherein the CD19×CD3 bispecific single chain antibody construct comprises a variable heavy chain anti-CD19 amino acid sequence set forth in SEQ ID NO: 3, a variable light chain anti-CD19 amino acid sequence set forth in SEQ ID NO: 5, a variable heavy chain anti-CD3 amino acid sequence set forth in SEQ ID NO: 7, and a variable light chain anti-CD3 amino acid sequence set forth in SEQ ID NO: 9.

19. The method of claim 1, wherein the CD19×CD3 bispecific single chain antibody construct is encoded by the nucleic acid sequence set forth in SEQ ID NO: 2; or, wherein the CD19×CD3 bispecific single chain antibody construct comprises the amino acid sequence set forth in SEQ ID NO: 1.

* * * * *

SEQUENCE LISTING

<160> NUMBER OF SEQ ID NOS: 22

<210> SEQ ID NO 1
<211> LENGTH: 498
<212> TYPE: PRT
<213> ORGANISM: Artificial Sequence
<220> FEATURE:
<223> OTHER INFORMATION: CD19xCD3 bispecific single chain antibody

<400> SEQUENCE: 1

```
Asp Ile Gln Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Asp
                245                 250                 255

Ile Lys Leu Gln Gln Ser Gly Ala Glu Leu Ala Arg Pro Gly Ala Ser
            260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
                325                 330                 335

Gln Leu Ser Ser Leu Thr Ser Glu Asp Ser Ala Val Tyr Tyr Cys Ala
            340                 345                 350

Arg Tyr Tyr Asp Asp His Tyr Cys Leu Asp Tyr Trp Gly Gln Gly Thr
```

```
                    355                 360                 365
Thr Leu Thr Val Ser Ser Val Glu Gly Gly Ser Gly Gly
        370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
                405                 410                 415

Ala Ser Ser Ser Val Ser Tyr Met Asn Trp Tyr Gln Gln Lys Ser Gly
                420                 425                 430

Thr Ser Pro Lys Arg Trp Ile Tyr Asp Thr Ser Lys Val Ala Ser Gly
                435                 440                 445

Val Pro Tyr Arg Phe Ser Gly Ser Gly Ser Gly Thr Ser Tyr Ser Leu
                450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
                485                 490                 495

Leu Lys

<210> SEQ ID NO 2
<211> LENGTH: 1494
<212> TYPE: DNA
<213> ORGANISM: Artificial Sequence
<220> FEATURE:
<223> OTHER INFORMATION: CD19xCD3 bispecific single chain antibody

<400> SEQUENCE: 2
gatatccagc tgacccagtc tccagcttct ttggctgtgt ctctagggca gagggccacc      60
atctcctgca aggccagcca agtgttgat tatgatggtg atagttattt gaactggtac     120
caacagattc caggacagcc acccaaactc ctcatctatg atgcatccaa tctagtttct     180
gggatcccac ccaggtttag tgcagtgggg tctgggacag acttcaccct caacatccat     240
cctgtggaga aggtggatgc tgcaacctat cactgtcagc aaagtactga ggatccgtgg     300
acgttcggtg agggaccaa gctcgagatc aaaggtggtg gtggttctgg cggcggcggc     360
tccggtggtg gtggttctca ggtgcagctg cagcagtctg ggctgagct ggtgaggcct     420 gggtcctcag tgaagatttc ctgcaaggct tctggctatg cattcagtag ctactggatg     480
aactgggtga agcagaggcc tggacagggt cttgagtgga ttggacagat ttggcctgga     540
gatggtgata ctaactacaa tggaaagttc aagggtaaag ccactctgac tgcagacgaa     600
tcctccagca cagcctacat gcaactcagc agcctagcat ctgaggactc tgcggtctat     660
ttctgtgcaa gacgggagac tacgacggta ggccgttatt actatgctat ggactactgg     720
ggccaaggga ccacggtcac cgtctcctcc ggaggtggtg gatccgatat caaactgcag     780
cagtcagggg ctgaactggc aagacctggg gcctcagtga agatgtcctg caagacttct     840
ggctacacct ttactaggta cacgatgcac tgggtaaaac agaggcctgg acagggtctg     900
gaatggattg gatacattaa tcctagccgt ggttatacta attacaatca gaagttcaag     960
gacaaggcca cattgactac agacaaatcc tccagcacag cctacatgca actgagcagc    1020
ctgacatctg aggactctgc agtctattac tgtgcaagat attatgatga tcattactgc    1080
cttgactact ggggccaagg caccactctc acagtctcct cagtcgaagg tggaagtgga    1140
ggttctggtg gaagtggagg ttcaggtgga gtcgacgaca ttcagctgac ccagtctcca    1200
gcaatcatgt ctgcatctcc aggggagaag gtcaccatga cctgcagagc cagttcaagt    1260
```

-continued

```
gtaagttaca tgaactggta ccagcagaag tcaggcacct cccccaaaag atggatttat   1320
gacacatcca aagtggcttc tggagtccct tatcgcttca gtggcagtgg gtctgggacc   1380
tcatactctc tcacaatcag cagcatggag gctgaagatg ctgccactta ttactgccaa   1440
cagtggagta gtaacccgct cacgttcggt gctgggacca agctggagct gaaa         1494
```

<210> SEQ ID NO 3
<211> LENGTH: 124
<212> TYPE: PRT
<213> ORGANISM: Artificial Sequence
<220> FEATURE:
<223> OTHER INFORMATION: VH anti CD19

<400> SEQUENCE: 3

```
Gln Val Gln Leu Gln Gln Ser Gly Ala Glu Leu Val Arg Pro Gly Ser
1               5                  10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
                100                 105                 110

Tyr Trp Gly Gln Gly Thr Thr Val Thr Val Ser Ser
        115                 120
```

<210> SEQ ID NO 4
<211> LENGTH: 372
<212> TYPE: DNA
<213> ORGANISM: Artificial Sequence
<220> FEATURE:
<223> OTHER INFORMATION: VH anti CD19

<400> SEQUENCE: 4

```
caggtgcagc tgcagcagtc tggggctgag ctggtgaggc ctgggtcctc agtgaagatt    60
tcctgcaagg cttctggcta tgcattcagt agctactgga tgaactgggt gaagcagagg   120
cctggacagg gtcttgagtg gattggacag atttggcctg gagatggtga tactaactac   180
aatggaaagt tcaagggtaa agccactctg actgcagacg aatcctccag cacagcctac   240
atgcaactca gcagcctagc atctgaggac tctgcggtct atttctgtgc aagacgggag   300
actacgacgg taggccgtta ttactatgct atggactact ggggccaagg gaccacggtc   360
accgtctcct cc                                                        372
```

<210> SEQ ID NO 5
<211> LENGTH: 111
<212> TYPE: PRT
<213> ORGANISM: Artificial Sequence
<220> FEATURE:
<223> OTHER INFORMATION: VL anti CD19

<400> SEQUENCE: 5

```
Asp Ile Gln Leu Thr Gln Ser Pro Ala Ser Leu Ala Val Ser Leu Gly
1               5                  10                  15
```

```
Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
 50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys
            100                 105                 110
```

<210> SEQ ID NO 6
<211> LENGTH: 333
<212> TYPE: DNA
<213> ORGANISM: Artificial Sequence
<220> FEATURE:
<223> OTHER INFORMATION: VL anti CD19

<400> SEQUENCE: 6

```
gatatccagc tgacccagtc tccagcttct ttggctgtgt ctctagggca gagggccacc     60
atctcctgca aggccagcca aagtgttgat tatgatggtg atagttattt gaactggtac    120
caacagattc caggacagcc acccaaactc ctcatctatg atgcatccaa tctagtttct    180
gggatcccac ccaggtttag tggcagtggg tctgggacag acttcaccct caacatccat    240
cctgtggaga aggtggatgc tgcaacctat cactgtcagc aaagtactga ggatccgtgg    300
acgttcggtg agggaccaa gctcgagatc aaa                                  333
```

<210> SEQ ID NO 7
<211> LENGTH: 119
<212> TYPE: PRT
<213> ORGANISM: Artificial Sequence
<220> FEATURE:
<223> OTHER INFORMATION: VH anti CD3

<400> SEQUENCE: 7

```
Asp Ile Lys Leu Gln Gln Ser Gly Ala Glu Leu Ala Arg Pro Gly Ala
  1               5                  10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
 50                  55                  60

Lys Asp Lys Ala Thr Leu Thr Thr Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115
```

<210> SEQ ID NO 8
<211> LENGTH: 357
<212> TYPE: DNA

<213> ORGANISM: Artificial Sequence
<220> FEATURE:
<223> OTHER INFORMATION: VH anti CD3

<400> SEQUENCE: 8

```
gatatcaaac tgcagcagtc aggggctgaa ctggcaagac ctggggcctc agtgaagatg      60
tcctgcaaga cttctggcta cacctttact aggtacacga tgcactgggt aaaacagagg     120
cctggacagg gtctggaatg gattggatac attaatccta gccgtggtta tactaattac     180
aatcagaagt tcaaggacaa ggccacattg actacagaca atcctccag cacagcctac       240
atgcaactga gcagcctgac atctgaggac tctgcagtct attactgtgc aagatattat     300
gatgatcatt actgccttga ctactgggc caaggcacca ctctcacagt ctcctca         357
```

<210> SEQ ID NO 9
<211> LENGTH: 106
<212> TYPE: PRT
<213> ORGANISM: Artificial Sequence
<220> FEATURE:
<223> OTHER INFORMATION: VL anti CD3

<400> SEQUENCE: 9

```
Asp Ile Gln Leu Thr Gln Ser Pro Ala Ile Met Ser Ala Ser Pro Gly
1               5                   10                  15
Glu Lys Val Thr Met Thr Cys Arg Ala Ser Ser Ser Val Ser Tyr Met
            20                  25                  30
Asn Trp Tyr Gln Gln Lys Ser Gly Thr Ser Pro Lys Arg Trp Ile Tyr
        35                  40                  45
Asp Thr Ser Lys Val Ala Ser Gly Val Pro Tyr Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Ser Asn Pro Leu Thr
                85                  90                  95
Phe Gly Ala Gly Thr Lys Leu Glu Leu Lys
            100                 105
```

<210> SEQ ID NO 10
<211> LENGTH: 318
<212> TYPE: DNA
<213> ORGANISM: Artificial Sequence
<220> FEATURE:
<223> OTHER INFORMATION: VL anti CD3

<400> SEQUENCE: 10

```
gacattcagc tgacccagtc tccagcaatc atgtctgcat ctccagggga gaaggtcacc      60
atgacctgca gagccagttc aagtgtaagt tacatgaact ggtaccagca gaagtcaggc    120
acctccccca aaagatggat ttatgacaca tccaaagtgg cttctggagt cccttatcgc    180
ttcagtggca gtgggtctgg gacctcatac tctctcacaa tcagcagcat ggaggctgaa    240
gatgctgcca cttattactg ccaacagtgg agtagtaacc cgctcacgtt cggtgctggg    300
accaagctgg agctgaaa                                                  318
```

<210> SEQ ID NO 11
<211> LENGTH: 10
<212> TYPE: PRT
<213> ORGANISM: artificial
<220> FEATURE:
<223> OTHER INFORMATION: CD3 CDR-H1

```
<400> SEQUENCE: 11

Gly Tyr Thr Phe Thr Arg Tyr Thr Met His
1               5                   10

<210> SEQ ID NO 12
<211> LENGTH: 17
<212> TYPE: PRT
<213> ORGANISM: artificial
<220> FEATURE:
<223> OTHER INFORMATION: CD3 CDR-H2

<400> SEQUENCE: 12

Tyr Ile Asn Pro Ser Arg Gly Tyr Thr Asn Tyr Asn Gln Lys Phe Lys
1               5                   10                  15

Asp

<210> SEQ ID NO 13
<211> LENGTH: 10
<212> TYPE: PRT
<213> ORGANISM: artificial
<220> FEATURE:
<223> OTHER INFORMATION: CD3 CDR-H3

<400> SEQUENCE: 13

Tyr Tyr Asp Asp His Tyr Cys Leu Asp Tyr
1               5                   10

<210> SEQ ID NO 14
<211> LENGTH: 10
<212> TYPE: PRT
<213> ORGANISM: artificial
<220> FEATURE:
<223> OTHER INFORMATION: CD3 CDR-L1

<400> SEQUENCE: 14

Arg Ala Ser Ser Ser Val Ser Tyr Met Asn
1               5                   10

<210> SEQ ID NO 15
<211> LENGTH: 7
<212> TYPE: PRT
<213> ORGANISM: artificial
<220> FEATURE:
<223> OTHER INFORMATION: CD3 CDR-L2

<400> SEQUENCE: 15

Asp Thr Ser Lys Val Ala Ser
1               5

<210> SEQ ID NO 16
<211> LENGTH: 9
<212> TYPE: PRT
<213> ORGANISM: artificial
<220> FEATURE:
<223> OTHER INFORMATION: CD3 CDR-L3

<400> SEQUENCE: 16

Gln Gln Trp Ser Ser Asn Pro Leu Thr
1               5

<210> SEQ ID NO 17
<211> LENGTH: 10
<212> TYPE: PRT
<213> ORGANISM: artificial
<220> FEATURE:
<223> OTHER INFORMATION: CD19 CDR-H1
```

-continued

```
<400> SEQUENCE: 17

Gly Tyr Ala Phe Ser Ser Tyr Trp Met Asn
1               5                   10

<210> SEQ ID NO 18
<211> LENGTH: 17
<212> TYPE: PRT
<213> ORGANISM: artificial
<220> FEATURE:
<223> OTHER INFORMATION: CD19 CDR-H2

<400> SEQUENCE: 18

Gln Ile Trp Pro Gly Asp Gly Asp Thr Asn Tyr Asn Gly Lys Phe Lys
1               5                   10                  15

Gly

<210> SEQ ID NO 19
<211> LENGTH: 15
<212> TYPE: PRT
<213> ORGANISM: artificial
<220> FEATURE:
<223> OTHER INFORMATION: CD19 CDR-H3

<400> SEQUENCE: 19

Arg Glu Thr Thr Thr Val Gly Arg Tyr Tyr Tyr Ala Met Asp Tyr
1               5                   10                  15

<210> SEQ ID NO 20
<211> LENGTH: 15
<212> TYPE: PRT
<213> ORGANISM: artificial
<220> FEATURE:
<223> OTHER INFORMATION: CD19 CDR-L1

<400> SEQUENCE: 20

Lys Ala Ser Gln Ser Val Asp Tyr Asp Gly Asp Ser Tyr Leu Asn
1               5                   10                  15

<210> SEQ ID NO 21
<211> LENGTH: 7
<212> TYPE: PRT
<213> ORGANISM: artificial
<220> FEATURE:
<223> OTHER INFORMATION: CD19 CDR-L2

<400> SEQUENCE: 21

Asp Ala Ser Asn Leu Val Ser
1               5

<210> SEQ ID NO 22
<211> LENGTH: 9
<212> TYPE: PRT
<213> ORGANISM: artificial
<220> FEATURE:
<223> OTHER INFORMATION: CD19 CDR-L3

<400> SEQUENCE: 22

Gln Gln Ser Thr Glu Asp Pro Trp Thr
1               5
```